US012630873B2

(12) United States Patent
O'Neil et al.

(10) Patent No.: US 12,630,873 B2
(45) Date of Patent: May 19, 2026

(54) UNIVERSAL LACTIC ACID BACTERIA QUANTIFICATION KIT FOR FERMENTATION MONITORING

(71) Applicant: NATIONAL AGRICULTURAL GENOTYPING CENTER, St. Louis, MO (US)

(72) Inventors: Megan Frances O'Neil, West Fargo, ND (US); Lisa Marie Piche, Frazee, MN (US)

(73) Assignee: National Agriculture Genotyping Center, St. Louis, MO (US)

( * ) Notice: Subject to any disclaimer, the term of this patent is extended or adjusted under 35 U.S.C. 154(b) by 786 days.

(21) Appl. No.: 17/046,660

(22) PCT Filed: Apr. 11, 2019

(86) PCT No.: PCT/US2019/027034
§ 371 (c)(1),
(2) Date: Oct. 9, 2020

(87) PCT Pub. No.: WO2019/200134
PCT Pub. Date: Oct. 17, 2019

(65) Prior Publication Data
US 2021/0172004 A1 Jun. 10, 2021

Related U.S. Application Data

(60) Provisional application No. 62/657,533, filed on Apr. 13, 2018.

(51) Int. Cl.
*C12Q 1/68* (2018.01)
*C12Q 1/686* (2018.01)
*C12Q 1/689* (2018.01)

(52) U.S. Cl.
CPC ............. *C12Q 1/686* (2013.01); *C12Q 1/689* (2013.01)

(58) Field of Classification Search
None
See application file for complete search history.

(56) References Cited

U.S. PATENT DOCUMENTS

| | | | |
|---|---|---|---|
| 6,759,233 B2 | 7/2004 | Leonard | |
| 7,547,526 B2 | 6/2009 | Ladisch et al. | |
| 2003/0050470 A1* | 3/2003 | An | C07H 21/00 |
| | | | 435/6.14 |
| 2012/0107799 A1 | 5/2012 | Daum | |
| 2012/0264126 A1 | 10/2012 | Johnson et al. | |
| 2015/0140583 A1 | 5/2015 | Hearn et al. | |
| 2016/0355871 A1 | 12/2016 | Want et al. | |
| 2017/0081704 A1 | 3/2017 | Weber et al. | |

FOREIGN PATENT DOCUMENTS

| | | |
|---|---|---|
| CN | 107523625 A | 12/2017 |
| EP | 3301189 A1 | 4/2018 |
| WO | 19960017949 A1 | 6/1996 |
| WO | 2013003262 A1 | 1/2013 |
| WO | 20130003262 A1 | 1/2013 |

OTHER PUBLICATIONS

Gadberry MD, Malcomber ST, Doust AN, Kellogg EA. Primaclade—a flexible tool to find conserved PCR primers across multiple species. Bioinformatics. Apr. 1, 2005; 21(7):1263-4. (Year: 2005).*

Genbank Accession No. AJ271383—Pediococcus inopinatus 16S rRNA gene, strain DSM 20285, submitted Jan. 27, 2000, retrieved on Mar. 12, 2023 from http://www.ncbi.nlm.nih.gov/nuccore/AJ271393). (Year: 2000).*

Genbank Accession No. AJ306297—Lactobacillus paraplantarum 16S rRNA gene, strain DSM 10667T, submitted Feb. 7, 2001, retrieved on Mar. 12, 2023 from http://www.ncbi.nlm.nih.gov/nuccore/AJ306297). (Year: 2001).*

Genbank Accession No. AM158250—Lactobacillus parabrevis 16S rRNA gene, strain LMG 11494, submitted Nov. 14, 2005, retrieved on Mar. 12, 2023 from http://www.ncbi.nlm.nih.gov/nuccore/AM158250). (Year: 2005).*

Genbank Accession No. AY035891—Weissella koreensis isolate S-5623 16S ribosomal RNA gene, partial sequence, submitted May 17, 2001, retrieved on Mar. 12, 2023 from http://www.ncbi.nlm.nih.gov/nuccore/AY035891). (Year: 2001).*

Genbank Accession No. AY035892—Weissella koreensis isolate S-5673 16S ribosomal RNA gene, partial sequence, submitted May 17, 2001, retrieved on Mar. 12, 2023 from http://www.ncbi.nlm.nih.gov/nuccore/AY035892). (Year: 2001).*

Genbank Accession No. EF120367—Lactobacillus brevis strain ATCC 14687 16S ribosomal RNA gene, partial sequence, submitted Nov. 14, 2006, retrieved on Mar. 12, 2023 from http://www.ncbi.nlm.nih.gov/nuccore/EF120367). (Year: 2006).*

SantaLucia Jr, John. Physical principles and visual-OMP software for optimal PCR design. PCR Primer Design. Humana Press, 2007: pp. 3-33. (Year: 2007).*

(Continued)

*Primary Examiner* — Gary Benzion
*Assistant Examiner* — Olayinka A Oyeyemi
(74) *Attorney, Agent, or Firm* — G. Harley Blosser; Sandberg Phoenix & von Gontard, PC

(57) ABSTRACT

Disclosed are universal LAB test kits, assays, apparatus and compositions for detecting and quantifying *Lactobacillus, Pediococcus* and *Weissella* bacteria, or combinations thereof that contaminate biological materials such as fermentation mashes for production of ethanol from a crop such as corn. The assays can be performed on-site by ethanol technicians having limited laboratory experience and are based on quantitative PCR (qPCR) methods. Primers and probes are described that specifically hybridize to a LAB bacteria gene. Also disclosed are sample preparation methods and apparatus, including a filtration syringe (100) that can increase sensitivity of the assays up to about 1000-fold compared to traditional sample preparation methods.

6 Claims, 3 Drawing Sheets

Specification includes a Sequence Listing.

(56)                References Cited

OTHER PUBLICATIONS

Bergsveinson et al., 2012. RT-qPCR analysis of putative beer-spoilage gene expression during growth of Lactobacillus brevis BSO 464 and Pediococcus claussenii ATCC BAA-344 T in beer. Applied microbiology and biotechnology, 96, pp. 461-470. (Year: 2012).*

Bohn et al., 2017. Isolation of lactic acid-forming bacteria from biogas plants. Journal of biotechnology, 244, pp. 4-15. (Year: 2017).*

Carraro et al., 2011. Comparison of culture-dependent and-independent methods for bacterial community monitoring during Montasio cheese manufacturing. Research in microbiology, 162(3), pp. 231-239. (Year: 2011).*

Gomez-Rojo et al., 2015. A novel real-time PCR assay for the specific identification and quantification of Weissella viridescens in blood sausages. International Journal of Food Microbiology, 215, pp. 16-24. (Year: 2015).*

Haarman M, Knol J. Quantitative real-time PCR analysis of fecal Lactobacillus species in infants receiving a prebiotic infant formula. Applied and Environmental Microbiology. 2006; 72:2359-2365. (Year: 2006).*

Mathys et al., 2007. Detection of the pediocin gene pedA in strains from human faeces by real-time PCR and characterization of Pediococcus acidilacticiUVA1. BMC biotechnology, 7(1), pp. 1-10. (Year: 2007).*

May et al., 2015. Design and application of a synthetic DNA standard for real-time PCR analysis of microbial communities in a biogas digester. Applied microbiology and biotechnology, 99, pp. 6855-6863. (Year: 2015).*

Park et al., 2010. Identification of the lactic acid bacteria in kimchi according to initial and over-ripened fermentation using PCR and 16S rRNA gene sequence analysis. Food Science and Biotechnology, 19, pp. 541-546. (Year: 2010).*

Pontonio et al., 2017. Sourdough authentication: Quantitative PCR to detect the lactic acid bacterial microbiota in breads. Scientific Reports, 7(1), p. 624. (Year: 2017).*

Stantscheff et al., 2014. Isolation and differentiation of methanogenic Archaea from mesophilic corn-fed on-farm biogas plants with special emphasis on the genus Methanobacterium. Applied microbiology and biotechnology, 98, pp. 5719-5735. (Year: 2014).*

Stevenson et al., 2006. Use of real time PCR to determine population profiles of individual species of lactic acid bacteria in alfalfa silage and stored corn stover. Appl Microbiol Biotechnol 71:329-338 (Year: 2006).*

Walter et al., 2001. Detection of Lactobacillus, Pediococcus, Leuconostoc, and Weissella species in human feces by using group-specific PCR primers and denaturing gradient gel electrophoresis. Applied and environmental microbiology, 67(6), pp. 2578-2585. (Year: 2001).*

Werning et al., 2006. Pediococcus parvulusgtf Gene Encoding the GTF Glycosyltransferase and Its Application for Specific PCR Detection of ß-d-Glucan-Producing Bacteria in Foods and Beverages. Journal of Food Protection, 69(1), pp. 161-169. (Year: 2006).*

Lee et al., 2017. Recovery of intact human norovirus from cabbage Kimchi stored at 4 C and 10 C during fermentation. LWT, 78, pp .258-264. (Year: 2017).*

Lim et al., Epub Dec. 12, 2017. Isolation of lactic acid bacteria starters from Jeung-pyun for sourdough fermentation. Food science and biotechnology, 2018, 27, pp. 73-78. (Year: 2017).*

European Search report to corresponding European application No. 19784695.1, mailed Dec. 16, 2021.

Brexo Ramon Peres et al: "Impact and significance of microbial contaminatic during fermentation for bioethanol production", Renewable and Sustainable Energy Reviews, vol. 73 , pp. 423-434, XP029951620, ISSN: 1364-0321, DOI: 10.1016/J.RSER.2017.01. 151.

Cappello Maria Stella et al: "Linking wine lactic acid bacteria diversity with wine aroma and flavour", International Journal of Food Microbiology, Elsevier BV, NL, vol. 243, Nov. 30, 2016 (Nov. 30, 2016), pp. 16-27, XP029892288, ISSN: 0168-1605, DOI: 10.1016/ J.IJFOODMICRO.2016.11.025.

Narva Ez-Zapata J A et al: "Culture-Independent Analysis of Lactic Acid Bacteria Diversity Associated with Mezcal Fermentation", Current Microbiology, Springer-Verlag, NE, vol. 61, No. 5, Apr. 10, 2010 (Apr. 10, 2010), pp. 444-450, XP019843498, ISSN: 1432-0991.

Robert H et al: "Biodiversity of lactic acid bacteria in French wheat sourdough determined by molecular characterization using species-specific PCR", International Journal of Food Microbiology, Elsevier BV, NL, vol. 135, No. 1, Sep. 30, 2009 (Sep. 30, 2009), pp. 53-59, XP026501092, ISSN: 0168-1605, DOI: 10.1016/J.IJFOODMICRO. 2009.07.006 [retrieved on Jul. 12, 2009].

Li Qing et al: "Bacterial Community Structure and Dynamics During Corn-Based Bioethanol Fermentation", Microbial Ecology, Springer US, New York, vol. 71, No. 2, Sep. 17, 2015 (Sep. 17, 2015), pp. 409-421, XP035870112, ISSN: 0095-3628, DOI: 10.1007/ S00248-015-0673-9 [retrieved on Sep. 17, 2015].

Yasushi Tanaka et al: "Monitoring of the microbial communities involved in the soy sauce manufacturing process py PCR-denaturing gradient gel electrophoresis", Food Microbiology., vol. 31, No. 1, Feb. 23, 2012 (Feb. 23, 2012), pp. 100-106, XP055526752, GB; ISSN: 0740-0020, DOI: 10.1016/j.fm.2012.02.005.

P. F. G Wolffs et al: "Direct Quantitation and Detection of Salmonellae in Biological Samples without Enrichment, Using Two-Step Filtration and Real-Time PCR", Applied and Environmental Microbiology, vol. 72, No. 6, Jun. 1, 2006 (Jun. 1, 2006), pp. 3896-3900.

International Search Report for PCT/US2019/027034 mailed Jun. 10, 2020.

Written Opinion for PCT/US2019/027034 mailed Jun. 10, 2020.

Zhu et al.; Complete Geneome Sequence and Transcriptomic Analysis of a Novel Marine Strain Bacillus Weihaiensis Reveals the Mechanmism of Brown Algae Degration, Scientific Reports, Nov. 30, 2016 (Nov. 30, 2016), vol. 6, No. 38248, pp. 1-10.

Chang et al.; Bacterial Contamination and Its Effects On Ethanol Fermentation; Journal Microbiology Biotechnology, 1995, vol. 5, pp. 309-314.

Skinner, K.A. and Leathers, T.D.; Bacterial Contaminants of Fuel Ethanol; Journal Industrial Microbiology and Biotechnology, 2004, vol. 31, pp. 401-408.

Lucerna et al.; Diversity of Lactic Acid Bacteria of the Bioethanol Process; BMC Microbiology, 2010, vol. 10, pp. 298-306.

Lewis, Scott; Options Expand for Effective Bacterial Control in Ethanol Production; Ethanol Producer Magazine, Dec. 2016 ed., pp. 44-47.

Beckner et al.; Microbial Contamination of Fuel Ethanol Fermentations; Letters in Applied Microbiology, 2011, vol. 53, pp. 387-394.

Henriques et al.; In Silico VS in Vitro Analysis of Primer Specificity for the Detection of Gardnerella Vaginalis, Atopobium Vaginae and Lactobacillus Spp.; 2012, BMC Research Notes 5, pp. 637.

Demkin et al., A Novel Real-Time PCR Assay for Highly Specific Detection and Quantification of Vaginal Lactobacilli; Molecular and Cellular Probes, 2017, vol. 32, pp. 33-39.

Baker et al., Review and Re-Analysis of Domain-Specific 16S Primers; Journal of Microbiological Methods, 2003, vol. 55, pp. 541-555.

Schwendimann Livia et al: "Development of a quantitative PCR assay for rapid detection of Lactobacillus plantarum and Lactobacillus fermentum in cocoa bean fermentation", Journal of Microbiological Methods, vol. 115, Aug. 1, 2015 (Aug. 1, 2015), pp. 94-99.

Muthaiyan Arunachalam et al: "Current perspectives on detection of microbial contamination in bioethanol fermentors", Bioresource Technology, Elsevier, Amsterdam, NL, vol. 101, No. 13, Dec. 1, 2009 (Dec. 1, 2009), pp. 5033-5042

Examination report in EP19784695.9 dated Apr. 9, 2025.

Chon et al., "Efficacy of Syringe Filtration for the Selective Isolation of Campylobacter from Chicken Carcass Rinse", Journal of Food Protection, vol. 80, No. 6, pp. 1050-1053, May 17, 2017 (May 17, 2017).

* cited by examiner

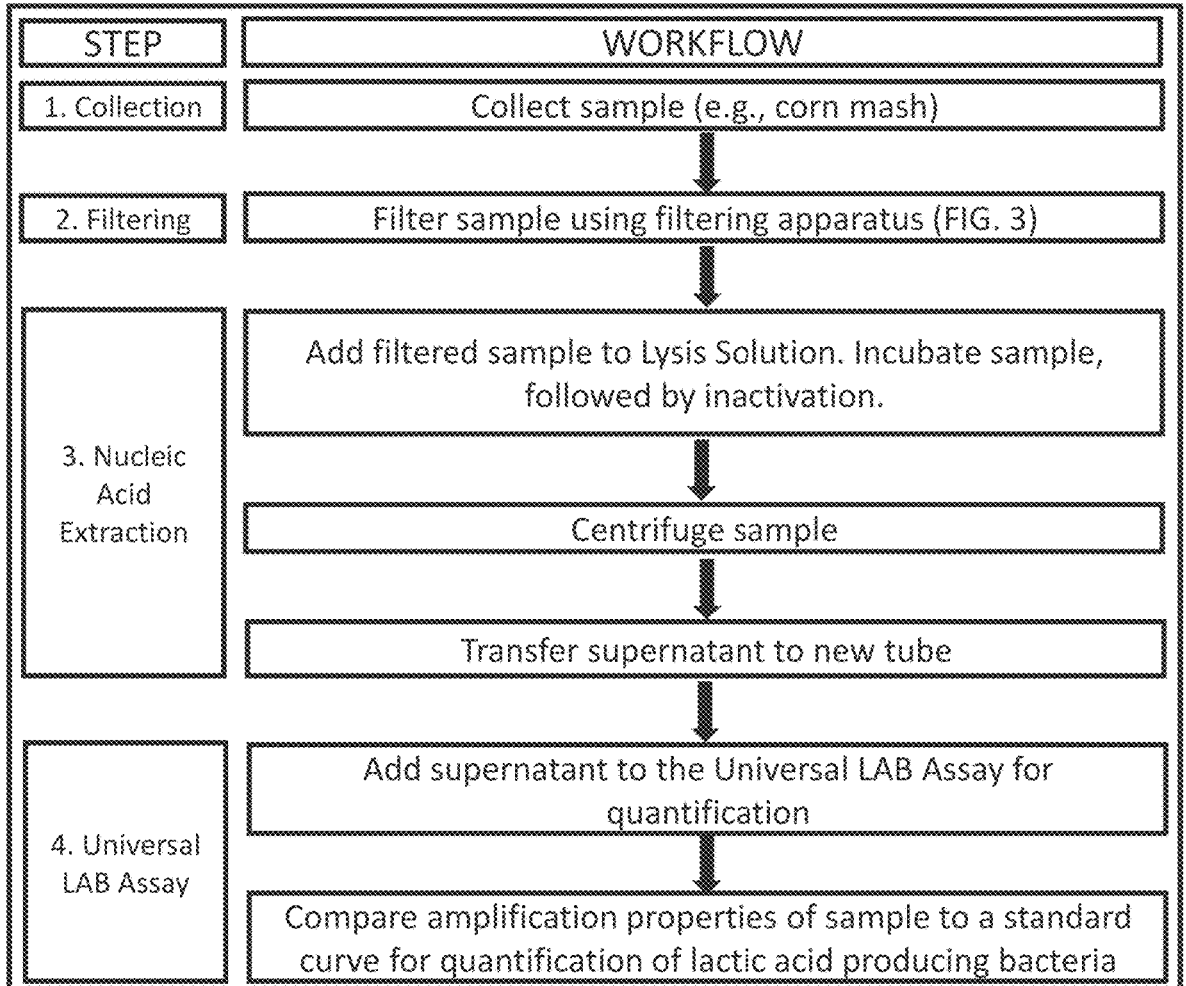

| STEP | WORKFLOW |
|------|----------|
| 1. Collection | Collect sample (e.g., corn mash) |
| 2. Filtering | Filter sample using filtering apparatus (FIG. 3) |
| 3. Nucleic Acid Extraction | Add filtered sample to Lysis Solution. Incubate sample, followed by inactivation. |
| | Centrifuge sample |
| | Transfer supernatant to new tube |
| 4. Universal LAB Assay | Add supernatant to the Universal LAB Assay for quantification |
| | Compare amplification properties of sample to a standard curve for quantification of lactic acid producing bacteria |

UNIVERSAL LACTIC ACID BACTERIA QUANTIFICATION KIT FOR FERMENTATION MONITORING

CROSS-REFERENCE TO RELATED APPLICATIONS

This application is the US National Stage under 35 USC § 371 of International Application No. PCT/US2019/027034 filed 11 Apr. 2019 which claims priority to U.S. Provisional App. No. 62/657,533 filed 13 Apr. 2018, respectively, all of which are incorporated herein by reference.

STATEMENT REGARDING FEDERALLY SPONSORED RESEARCH

Not Applicable.

SEQUENCE LISTING STATEMENT

The official copy of the sequence listing is submitted electronically via EFS-Web as an ASCII formatted sequence listing with a file named "nagcf464wo.txt", created on Apr. 11, 2019, and having a size of "2,190 bytes" and is filed concurrently with the specification. The sequence listing contained in this ASCII formatted document is part of the specification and is herein incorporated by reference in its entirety.

FIELD OF THE INVENTION

The subject matter herein relates generally to kits, methods, apparatuses, assay components and compositions useful to detect and quantify three of the major groups of lactic acid producing bacteria (LAB) from along or within a fermentation production line.

BACKGROUND OF THE INVENTION

The production of ethanol from agricultural sources, such as the production of ethanol from corn, involves fermentation by microorganisms. This, for example, can involve fermentation of a corn mash by yeast. However, species of *Lactobacillus*, a Gram-positive LAB can frequently account for up to 60% of bacterial contamination in wet mill operations and up to 87% of bacterial contamination in the more common dry mill process. *Pediococcus* and *Weissella*, are other LAB of secondary and tertiary concern as contaminants; they, in addition to *Lactobacillus*, together make up the three most common contaminants found in ethanol plants and can significantly reduce ethanol production. Over 20 different *Lactobacillus* species, alone, are commonly found as contaminants within ethanol fermentations (Chang, I., et al., J Microbiology Biotechnology, 1995, 5, 309-314; Skinner, K. A. and Leathers, T. D., J Industrial Microbiology and Biotechnology, 2004, 31, 401-408; Lucena, B. T., et al., BMC Microbiology, 2010, 10, 298-306). Thus, there is a need to monitor ethanol fermentations such as fermenting corn mashes for such contaminating *Lactobacillus, Pediococcus* and *Weissella* bacteria. For example, if *Lactobacillus* or other LAB levels are too high during an ethanol production fermentation, "(e)xcessive bacteria can cost as much as $190,000 if a single fermenter is entirely lost." (Lewis, Ethanol Producer Magazine, December, 2016 ed., 44-47). As further reported by M. Beckner (2011), "Microbial contamination is a pervasive problem in any ethanol fermentation system. These infections can at minimum affect the efficiency of the fermentation and at their worst lead to stuck fermentations causing plants to shut down for cleaning before beginning anew. These delays can result in costly loss of time as well as lead to an increased cost of the final product. LAB are the most common bacterial contaminants found in ethanol production facilities and have been linked to decreased ethanol production during fermentation" (M. Beckner, et al., Letters in Applied Microbiology, 2011, 53, 387-394).

Current techniques for detecting and quantifying LAB suffer from a variety of deficiencies. In general, they provide only very limited discriminatory power, particularly for a large and phylogenetically complicated taxon such as the genus *Lactobacillus* (Henriques, A., et al., 2012, *BMC Research Notes* 5, 637; Baker, G. C., et al., 2003, *J. Microbiological Methods*, 55, 541e555). Second, the current testing platforms are frequently known to lead to an over- or underestimation of the abundance of many LAB species as certain species possess different copy numbers of the target genes (Demkin, V. V., et al., *Molecular and Cellular Probes*, 2017, 32, 33-39). Additionally, many of the tests are unable to detect a number of contaminant species within the lactic acid bacteria group commonly present in the typical ethanol fermentation process such as *L. brevis, L. casei, L. diolivorans*-like, *L. ferintoshensis* (aka *L. parabuchneri*), *L. hilgardii, L. lindneri, L. manihotivorans, L. nagelii, L. paracasei* subsp. *paracasei, L. rhamnosus*, and *L. vini*. There is a lack of detection and quantification methods that can broadly identify diverse species of *Lactobacillus* and other LAB such as *Pediococcus* and *Weissella* that commonly contaminate corn mashes or other fermentation mixtures during the ethanol production process. Finally, LAB detection kits currently on the market require the use of a clear liquid, e.g., beer, or a sample diluted in buffer prior to centrifugation and processing of the resulting pellet. Corn-based ethanol fermentation tank samples consist of a thick slurry of ground-up corn and water mixed together to form a "mash". The mash sample matrix is difficult to process, and its centrifugation can result in a very large pellet that will often clog the existing column and filter based systems leading to unreliable results or even possibly a complete loss of signal.

New methods of detecting lactic acid bacterial contamination are needed, including new kits, methods, apparatuses and compositions used in preparing mash and other fermentation samples for broadly detecting and quantifying diverse species and genera of contaminating LAB.

SUMMARY OF THE INVENTION

Applicants have invented universal lactic acid bacteria kits, methods, and compositions and apparatuses therefor, which address the above-described needs by serving to broadly detect and quantify the three major groups of LAB, which include but are not limited to over thirty species of *Lactobacillus, Pediococcus* and *Weissella*, the most common contaminants found in ethanol fermentation.

Also provided as a part of this invention are filtration apparatuses for enhanced purification of fermentation samples. In one preferred embodiment of the filtration apparatus of the invention, a barrel and plunger combination is provided, such as one defining an interior space configured for containing the fermentation sample, such as a syringe-type filtration apparatus is provided. In this embodiment, the apparatus contains a filter, sized to allow LAB cells of interest to pass through pores in the filter, but to substantially screen out bulk organic matter, to form an LAB-cell containing filtrate. The apparatus as thus embodied includes a receptacle portion located adjacent to the filter for receiving the LAB-cell containing filtrate, or a conduit for transfer of the LAB-cell containing filtrate after its passage through the filter to such a receptacle. Also included in the filtration apparatus of this embodiment is a device attached or integral to the plunger for urging the fermentation sample toward the screen mesh and facilitating removal of any excessive starch-releasing particles from the fermentation sample.

Also provided are a rapid nucleic acid extraction method and a real-time PCR assay for broad-scale LAB detection and quantification, which can be undertaken with great sensitivity, yet is easily implemented and interpreted without a great deal of training or prior experience with molecular assays.

Specifically provided are primers, probes, kits, and methods for DNA extraction and the subsequent detection and quantification of *Lactobacillus, Pediococcus* and *Weissella*, or some sub-combination of their nucleic acids, in a test sample. Such test samples may be obtained from different substrates and throughout the fermentation process, including, but not limited to, yeast propagation, processed condensate, and beer well. In certain preferred embodiments, the kits can consist of, e.g., sample extraction and LAB PCR assay reagents or multiplex arrays made in a ready-to-use format to ensure a high degree of consistency from sample to sample. In some embodiments, aliquots of the reagents are provided. This standardized, and in certain embodiments, automated approach, can minimize pipetting and other non-standardized steps and help to provide increased repeatability and reproducibility of test results from less experienced users having limited to no molecular biology experience.

Also among the objects of the invention is the provision of kits, methods, apparatuses, and compositions which assist the ethanol industry and others involved in fermentation processing by increasing their ability to track levels of LAB during the fermentation process. Thus, additional objects of the invention include assisting to reduce ethanol losses, e.g., by aiding in identifying locations in an ethanol facility where bacterial build-up may be occurring, assisting in monitoring decontamination procedures and providing data for developing more precise and prescribed regimes for antibiotic use, thus helping to minimize unwanted antibiotic residues in co-products. As overuse of antibiotics has been shown to produce increasingly antibiotic-resistant strains of bacteria, the invention has the added benefit of slowing the development of such bacteria.

According to another aspect of the invention, a method for quantification of LAB in a sample of interest is provided. The method includes the steps of collecting a sample of interest, filtering the LAB to be quantified from the sample of interest by passing the sample through a filtration device configured to remove bulk organic matter from the LAB to create a LAB-containing sample filtrate. The method provides information for conducting a nucleic acid extraction of the LAB by lysing cells of the LAB to achieve a LAB-containing DNA supernatant. Additionally, a universal LAB assay as described herein is configured to target particular genera and species of interest so that they can be detected and substantially quantified to a highly sensitive degree of quantitative certainty, as demonstrated in the below provided experimental examples.

According to another aspect of the invention, qPCR-based assays are provided for the detection and quantification of over 30 different lactic acid bacterial species commonly found as contaminants of ethanol production and other fermentation systems such as, for example, fermentations of corn mash, wheat mash, beer, and sauerkraut.

With regard to an additional aspect, applicants have developed a system, including an apparatus and method, for preparing fermentation mixtures such as mash samples for use in assays for detecting LAB. The methods of the system can be used to detect LAB from a variety of sample sources, such as, but not limited to corn mash undergoing fermentation, bee populations, soil, and agricultural crops. In the system of the invention, particles that are slightly larger than most bacteria can be sieved out. In their methods, a filtrate can be collected which can be subjected to molecular analysis, such as a PCR analysis, for detection of contaminating LAB. When used in conjunction with a universal LAB PCR-based assay described herein, contaminating LAB in a sample can be detected and quantified.

In accordance with another aspect of the invention, novel DNA oligonucleotides are provided and are used as probes, forward primers and reverse primers as set out more fully hereinafter.

Other aspects of the invention will be apparent to those skilled in the art in light of the following description and claims.

BRIEF DESCRIPTION OF THE DRAWINGS

FIG. 1 is a flow chart showing an embodiment of the method of detection and quantification of LAB according to the invention.

FIG. 3A is a somewhat diagrammatic exploded front elevation view of an embodiment of a filtration syringe according to the invention.

FIG. 3B is a somewhat diagrammatic front elevation view of the assembled filtration syringe of FIG. 3A.

Figures 2A, 2B, 2C, 2D:
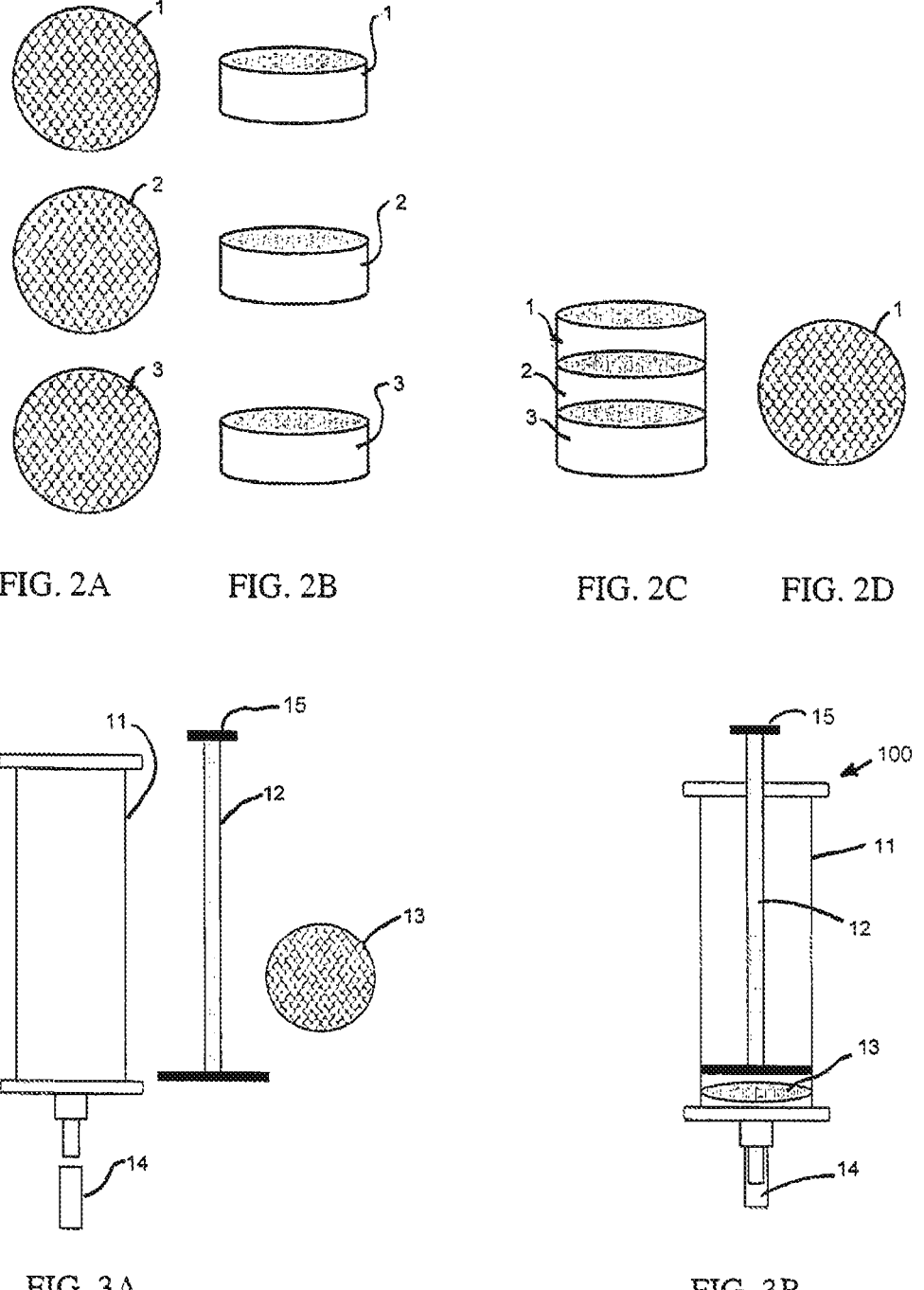
FIG. 2A is a somewhat diagrammatic exploded view in top plane of a pan sieve filter system according to the invention.
FIG. 2B is a somewhat diagrammatic exploded view in side elevation of the pan sieve filter system of FIG. 2A.
FIG. 2C is a somewhat diagrammatic top plane view of the assembled pan sieve filter system of FIGS. 2A and 2B.
FIG. 2D is a somewhat diagrammatic view in side elevation of the pan sieve filter system of FIGS. 2A-C.

ABBREVIATIONS bps: base pairs
CFU: Colony forming unit
CFU/ml: Colony forming unit per milliliter
Ct: Cycle threshold, the number of cycles required for the fluorescent signal to cross the threshold, exceeding background level
CXR: Carboxy-X-rhodamine, reference dye
DNA: Deoxyribonucleic acid
HPLS: High performance liquid chromatography
IDT: Integrated DNA Technologies
LAB: Lactic acid bacteria
PCR: Polymerase chain reaction
qPCR: Quantitative polymerase chain reaction

DESCRIPTION OF THE PREFERRED EMBODIMENT

The following detailed description illustrates the claimed invention by way of example and not by way of limitation.

The description enables one skilled in the art to make and use the invention, describes several embodiments, adaptations, variations, alternatives, and uses of the claimed invention, including what is presently believed to be the best mode of carrying out the claimed invention. Additionally, it is to be understood that the claimed invention is not limited in its application to the details of construction and the arrangement of components set forth in the following description or illustrated in the drawings. The claimed invention is capable of other embodiments and of being practiced or being carried out in various ways. Also, it is to be understood that the phraseology and terminology used herein is for the purpose of description and should not be regarded as limiting.

As indicated in the flow chart depicted in FIG. 1, a preferred embodiment of the LAB detection and quantification procedure of the invention brings together certain apparatus and compositions to readily provide a sensitive determination of the presence and quantity of LAB genera and species of interest in a corn to ethanol or other fermentation process.

According to a preferred embodiment, a sample of interest is collected from anywhere within the production pipeline, using the equipment, compositions and methods provided for herein. In a preferred embodiment, the first step includes a separation of the bulk organic matter by the mechanical separation through a mesh screen.

In various embodiments, the present teachings include methods of preparing a biological sample for a qPCR analysis, involving substantial purification of the initially collected sample and ultimate separation of the target nucleic acids of interest of the contaminating LAB species from other materials in a fermentation sample which serve to interfere with such detection and especially, quantification. Referring to FIGS. 2A-2D, an embodiment of a multisieve filtration apparatus (or a combination of separately stacked filters of various dimensions) is shown. In various configurations, these methods can comprise: i) passing a biological sample through a filter 1 with a limiting pore size thereby forming a first filtrate; ii) passing the first filtrate through a filter 2 with a limiting pore size thereby forming a second filtrate; and iii) passing the second filtrate through a filter 3 with a limiting pore size thereby forming a third filtrate. The pore sizes of the filters are graduated, with the limiting pore size of the first filter being largest. In other configurations, the first and second filtrates are collected and segregated before they are filtered further. In various configurations, the preparation can further comprise iv) forming a sample of the third filtrate into a pellet. In various configurations, the forming of a sample of the third filtrate into a pellet can comprise subjecting the sample to centrifugation. In various configurations, a method of preparing a sample can further comprise subjecting the pellet to proteolytic lysis.

In various configurations, the first filter can have a pore size of 500 μm to 1000 μm. In various configurations, the first filter can have a pore size of 510 μm to 990 μm, 520 μm to 980 μm, 530 μm to 970 μm, 540 to 960 μm, 550 to 950 μm, 560 to 940 μm, 570 to 930 μm, 580 to 920 μm, 590 to 910 μm, 600 to 900 μm, 610 to 890 μm, 620 to 880 μm, 630 to 870 μm, 440 to 860 μm, 650 to 850 μm, 660 to 840 μm, 670 to 830 μm, 680 to 820 μm, 690 to 810 μm, 700 to 800 μm, 710 to 790 μm, 720 to 780 μm, 730 to 770 μm, or 740 to 760 μm. In various configurations, the first filter can have a pore size of 500 μm-510 μm, 510 μm-520 μm, 520 μm-530 μm, 530 μm-540 μm, 540 μm-550 μm, 550 μm-560 μm, 560 μm-570 μm, 570 μm-580 μm, 580 μm-590 μm, 590-600 μm, 600-610 μm, 610-620 μm, 620 μm-630 μm, 630 μm-640 μm, 640 μm-650 μm, 650 μm-660 μm, 660 μm-670 μm, 670 μm-680 μm, 680 μm-690 μm, 690 μm-700 μm, 700 μm-710 μm, 710 μm-720 μm, 720 μm-730 μm, 730 μm-740 μm, 740 μm-750 μm, 750 μm-760 μm, 760 μm-770 μm, 770 μm-780 μm, 780 μm-790 μm, 790 μm-800 μm, 800 μm-810 μm, 810 μm-820 μm, 820 μm-830 μm, 830 μm-840 μm, 840 μm-850 μm, 850 μm-860 μm, 860 μm-870 μm, 870 μm-880 μm, 880 μm-890 μm, 890 μm-900 μm, 900 μm-910 μm, 910 μm-920 μm, 920 μm-930 μm, 930 μm-940 μm, 940 μm-950 μm, 950 μm-960 μm, 960 μm-970 μm, 970 μm-980 μm, 980 μm-990 μm, or 990 μm-1000 μm.

In various configurations, the second filter can have a pore size of 200 μm to 600 μm. In various configurations, the second filter can have a pore size of 210 μm to 590 μm, 220 μm to 580 μm, 230 μm to 570 μm, 240 μm to 560 μm, 250 μm to 550 μm, 260 μm to 540 μm, 270 μm to 530 μm, 280 μm to 520 μm, 290 μm to 510 μm, 300 μm to 500 μm, 310 μm to 490 μm, 320 μm to 480 μm, 330 μm to 470 μm, 340 μm to 460 μm, 350 μm to 450 μm, 360 μm to 440 μm, 370 μm to 430 μm, 380 μm to 420 μm, or 390 μm to 410 μm. In various configurations, the second filter can have a pore size of 200 μm-210 μm, 210 μm-220 μm, 220 μm-230 μm, 230 μm-240 μm, 240 μm-250 μm, 250 μm-260 μm, 260 μm-270 μm, 270 μm-280 μm, 280 μm-290 μm, 290 μm-300 μm, 292 μm-302 μm, 295 μm-305 μm, 297 μm-307 μm, 300 μm-310 μm, 310 μm-320 μm, 320 μm-330 μm, 330 μm-340 μm, or 340 μm-350 μm, 350 μm-360 μm, 360 μm-370 μm, 370 μm-380 μm, 380 μm-390 μm, 390 μm-400 μm, 400 μm-410 μm, 410 μm-420 μm, 420 μm-430 μm, 430 μm-440 μm, 440 μm-450 μm, 450 μm-460 μm, 460 μm-470 μm, 470 μm-480 μm, 480 μm-490 μm, 490 μm-500 μm, 500 μm-510 μm, 510 μm-520 μm, 520 μm-530 μm, 530 μm-540 μm, 540 μm-550 μm, 550 μm-560 μm, 560 μm-570 μm, 570 μm-580 μm, 580 μm-590 μm, or 590 μm-600 μm.

In various configurations, the third filter can have a pore size of 100 μm to 300 μm. In various configurations, the third filter can have a pore size of 110 μm to 290 μm, 120 μm to 280 μm, 130 μm to 270 μm, 140 μm to 260 μm, 150 μm to 250 μm, 160 μm to 240 μm, 170 μm to 230 μm, 180 μm to 220 μm, or 190 μm to 210 μm. In various configurations, the third filter can have a pore size of 100 μm-110 μm, 110 μm-120 μm, 120 μm-130 μm, 130 μm-140 μm, 140 μm-150 μm, 145 μm-155 μm, 150 μm-160 μm, 160 μm-170 μm, 170 μm-180 μm, 180 μm-190 μm, 190 μm-200 μm, 200 μm-210 μm, 210 μm-220 μm, 220 μm-230 μm, 230 μm-240 μm, 240 μm-250 μm, 250 μm-260 μm, 260 μm-270 μm, 270 μm-280 μm, 280 μm-290 μm, 290 μm-300 μm.

In various configurations, methods of quantifying a microorganism in a biological mixture such as a corn mash can comprise passing a biological mixture through three or more filters, such as, for example: i) passing a biological mixture through a first filter having a limited pore size, thereby forming a first filtrate; ii) passing the first filtrate through a second filter having a limited pore size, thereby forming a second filtrate; and iii) passing the second filtrate through a third filter having a limited pore size, thereby forming a third filtrate; iv) forming a sample of the third filtrate into a pellet; v) subjecting the pellet to a homogenization procedure; and vi) extracting DNA from the pellet by a DNA miniprep extraction procedure; and vii) subjecting the DNA to a qPCR analysis. In various configurations, each filter can be independently selected from the group consisting of a pan filter, a spin filter, and a spin basket filter. In various configurations, the forming a final filtrate into a pellet can comprise subjecting the third filtrate to centrifugation. In various configurations, the forming the third filtrate into a pellet can comprise subjecting the filtrate to centrifugation. In various configurations, the pellet can be resuspended; a resuspended pellet can be subjected to a DNA extraction. In some configurations, the extracted DNA can be subjected to a qPCR-based analysis.

In various configurations, e.g., wherein three filters are used, the first filter can have a pore size of 500 μm to 1000 μm. In various configurations, the first filter can have a pore size of 510 μm to 990 μm, 520 μm to 980 μm, 530 μm to 970 μm, 540 to 960 μm, 550 to 950 μm, 560 to 940 μm, 570 to 930 μm, 580 to 920 μm, 590 to 910 μm, 600 to 900 μm, 610 to 890 μm, 620 to 880 μm, 630 to 870 μm, 440 to 860 μm, 650 to 850 μm, 660 to 840 μm, 670 to 830 μm, 680 to 820 μm, 690 to 810 μm, 700 to 800 μm, 710 to 790 μm, 720 to 780 μm, 730 to 770 μm, or 740 to 760 μm. In various configurations, the first filter can have a pore size of 500 μm-510 μm, 510 μm-520 μm, 520 μm-530 μm, 530 μm-540 μm, 540 μm-550 μm, 550 μm-560 μm, 560 μm-570 μm, 570 μm-580 μm, 580 μm-590 μm, 590-600 μm, 600-610 μm, 610-620 μm, 620 μm-630 μm, 630 μm-640 μm, 640 μm-650 μm, 650 μm-660 μm, 660 μm-670 μm, 670 μm-680 μm, 680 μm-690 μm, 690 μm-700 μm, 700 μm-710 μm, 710 μm-720 μm, 720 μm-730 μm, 730 μm-740 μm, 740 μm-750 μm, 750 μm-760 μm, 760 μm-770 μm, 770 μm-780 μm, 780 μm-790 μm, 790 μm-800 μm, 800 μm-810 μm, 810 μm-820 μm, 820 μm-830 μm, 830 μm-840 μm, 840 μm-850 μm, 850 μm-860 μm, 860 μm-870 μm, 870 μm-880 μm, 880 μm-890 μm, 890 μm-900 μm, 900 μm-910 μm, 910 μm-920 μm, 920 μm-930 μm, 930 μm-940 μm, 940 μm-950 μm, 950 μm-960 μm, 960 μm-970 μm, 970 μm-980 μm, 980 μm-990 μm, or 990 μm-1000 μm.

In various configurations of the above embodiment, the second filter can have a pore size of 200 μm to 600 μm. In various configurations, the second filter can have a pore size of 210 μm to 590 μm, 220 μm to 580 μm, 230 μm to 570 μm, 240 μm to 560 μm, 250 μm to 550 μm, 260 μm to 540 μm, 270 μm to 530 μm, 280 μm to 520 μm, 290 μm to 510 μm, 300 μm to 500 μm, 310 μm to 490 μm, 320 μm to 480 μm, 330 μm to 470 μm, 340 μm to 460 μm, 350 μm to 450 μm, 360 μm to 440 μm, 370 μm to 430 μm, 380 μm to 420 μm, or 390 μm to 410 μm. In various configurations, the second filter can have a pore size of 200 μm-210 μm, 210 μm-220 μm, 220 μm-230 μm, 230 μm-240 μm, 240 μm-250 μm, 250 μm-260 μm, 260 μm-270 μm, 270 μm-280 μm, 280 μm-290 μm, 290 μm-300 μm, 292 μm-302 μm, 295 μm-305 μm, 297 μm-307 μm, 300 μm-310 μm, 310 μm-320 μm, 320 μm-330 μm, 330 μm-340 μm, or 340 μm-350 μm, 350 μm-360 μm, 360 μm-370 μm, 370 μm-380 μm, 380 μm-390 μm, 390 μm-400 μm, 400 μm-410 μm, 410 μm-420 μm, 420 μm-430 μm, 430 μm-440 μm, 440 μm-450 μm, 450 μm-460 μm, 460 μm-470 μm, 470 μm-480 μm, 480 μm-490 μm, 490 μm-500 μm, 500 μm-510 μm, 510 μm-520 μm, 520 μm-530 μm, 530 μm-540 μm, 540 μm-550 μm, 550 μm-560 μm, 560 μm-570 μm, 570 μm-580 μm, 580 μm-590 μm, or 590 μm-600 μm.

In various configurations of the above embodiment, the third filter can have a pore size of 100 μm to 300 μm. In various configurations, the third filter can have a pore size of 110 μm to 290 μm, 120 μm to 280 μm, 130 μm to 270 μm, 140 μm to 260 μm, 150 μm to 250 μm, 160 μm to 240 μm, 170 μm to 230 μm, 180 μm to 220 μm, or 190 μm to 210 μm. In various configurations, the third filter can have a pore size of 100 μm-110 μm, 110 μm-120 μm, 120 μm-130 μm, 130 μm-140 μm, 140 μm-150 μm, 145 μm-155 μm, 150 μm-160 μm, 160 μm-170 μm, 170 μm-180 μm, 180 μm-190 μm, 190 μm-200 μm, 200 μm-210 μm, 210 μm-220 μm, 220 μm-230

μm, 230 μm-240 μm, 240 μm-250 μm, 250 μm-260 μm, 260 μm-270 μm, 270 μm-280 μm, 280 μm-290 μm, 290 μm-300 μm.

In various configurations, the biological sample can be a fermentation sample. In various configurations, the biological sample can be a corn mash. In various configurations, the microorganism can be of the genera *Lactobacillus, Pediococcus* or *Weissella*. In various configurations, but not limited to, the *Lactobacillus* can be selected from the group consisting of *L. acidophilus, L. amylovorus, L. brevis, L. buchneri, L. casei, L. crispatus, L. delbrueckii* subsp. *delbrueckii, L. delbrueckii* subsp. *lactis, L. diolivorans*-like, *L. ferintoshensis* (aka *parabuchneri*), *L. fermentum, L. gasseri, L. helveticus, L. hilgardii, L. lindneri, L. manihotivorans, L. mucosae, L. nagelii, L. paracasei* subsp. *paracasei, L. pentosus, L. plantarum, L. reuteri, L. rhamnosus, L. salivarius* subsp. *salivarius, L. vini* and any combination thereof. In various configurations, but not limited to, the *Pediococcus* bacterial species can be selected from the group consisting of *P. acidilactici, P. damnosus, P. inopinatus, P. parvulus*, and *P. pentosaceus* and any combination thereof. In various configurations, but not limited to, the *Weissella* bacterial species can be selected from the group consisting of *W. confusa, W. paramesenteroides*, and *W. viridescens* and any combination thereof.

In various configurations, the biological mixture can be at least 1 ml in volume up to 2000 ml in volume. In various configurations, the biological mixture can be 1 ml-5 ml, 5 ml-10 ml, 10 ml-15 ml, 15 ml-20 ml, 20 ml-25 ml, 25 ml-30 ml, 35 ml-40 ml, 40 ml-45 ml, 45 ml-50 ml, 50 ml-60 ml, 60 ml-70 ml, 70 ml-80 ml, 80 ml-90 ml, 90 ml-100 ml, 100 ml-125 ml, 125 ml-150 ml, 150 ml-175 ml, 175 ml-200 ml, 200 ml-225 ml, 225 ml-250 ml, 250 ml-275 ml, 275 ml-300 ml, 300 ml-325 ml, 325 ml-350 ml, 350 ml-375 ml, 375 ml-400 ml, 400 ml-425 ml, 425 ml-450 ml, 450 ml-475 ml, 475 ml-500 ml, 500 ml-525 ml, 525 ml-550 ml, 550 ml-575 ml, 575 ml-600 ml, 600 ml-625 ml, 625 ml-650 ml, 650 ml-675 ml, 675 ml-700 ml, 700 ml-725 ml, 725 ml-750 ml, 750 ml-775 ml, 775 ml-800 ml, 800 ml-825 ml, 825 ml-850 ml, 850 ml-875 ml, 875 ml-900 ml, 900 ml-925 ml, 925 ml-950 ml, 950 ml-975 ml, 975 ml-1000 ml, 1000 ml-1025 ml, 1025 ml-1050 ml, 1050 ml-1075 ml, 1075 ml-1100 ml, 1100 ml-1125 ml, 1125 ml-1150 ml, 1150 ml-1175 ml, 1175 ml-1200 ml, 1200 ml-1225 ml, 1225 ml-1250 ml, 1250 ml-1275 ml, 1275 ml-1300 ml, 1300 ml-1325 ml, 1325 ml-1350 ml, 1350 ml-1375 ml, 1375 ml-1400 ml, 1400 ml-1425 ml, 1425 ml-1450 ml, 1450 ml-1475 ml, 1475 ml-1500 ml, 1500 ml-1525 ml, 1525 ml-1550 ml, 1550 ml-1575 ml, 1575 ml-1600 ml, 1600 ml-1625 ml, 1625 ml-1650 ml, 1650 ml-1675 ml, 1675 ml-1700 ml, 1700 ml-1725 ml, 1725 ml-1750 ml, 1750 ml-1775 ml, 1775 ml-1800 ml, 1800 ml-1825 ml, 1825 ml-1850 ml, 1850 ml-1875 ml, 1875 ml-1900 ml, 1900 ml-1925 ml, 1925 ml-1950 ml, 1950 ml-1975 ml, 1975 ml-2000 ml.

In some embodiments, in methods of the present teachings, a corn mash can be filtered through one, two, three, or more filters prior to DNA extraction. In some configurations, the corn mash can be passed through a first filter with a limited pore size, thereby forming a first filtrate. The resulting first filtrate can then be passed through a second filter with a limited pore size, thereby forming a second filtrate. The resulting second filtrate can then be passed through a third filter with a limited pore size, thereby forming a third filtrate.

In various configurations, the first filter can have a pore size of 500 μm to 1000 μm. In various configurations, the first filter can have a pore size of 510 μm to 990 μm, 520 μm to 980 µm, 530 µm to 970 µm, 540 to 960 µm, 550 to 950 µm, 560 to 940 µm, 570 to 930 µm, 580 to 920 µm, 590 to 910 µm, 600 to 900 µm, 610 to 890 µm, 620 to 880 µm, 630 to 870 µm, 440 to 860 µm, 650 to 850 µm, 660 to 840 µm, 670 to 830 µm, 680 to 820 µm, 690 to 810 µm, 700 to 800 µm, 710 to 790 µm, 720 to 780 µm, 730 to 770 µm, or 740 to 760 µm. In various configurations, the first filter can have a pore size of 500 µm-510 µm, 510 µm-520 µm, 520 µm-530 µm, 530 µm-540 µm, 540 µm-550 µm, 550 µm-560 µm, 560 µm-570 µm, 570 µm-580 µm, 580 µm-590 µm, 590-600 µm, 600-610 µm, 610-620 µm, 620 µm-630 µm, 630 µm-640 µm, 640 µm-650 µm, 650 µm-660 µm, 660 µm-670 µm, 670 µm-680 µm, 680 µm-690 µm, 690 µm-700 µm, 700 µm-710 µm, 710 µm-720 µm, 720 µm-730 µm, 730 µm-740 µm, 740 µm-750 µm, 750 µm-760 µm, 760 µm-770 µm, 770 µm-780 µm, 780 µm-790 µm, 790 µm-800 µm, 800 µm-810 µm, 810 µm-820 µm, 820 µm-830 µm, 830 µm-840 µm, 840 µm-850 µm, 850 µm-860 µm, 860 µm-870 µm, 870 µm-880 µm, 880 µm-890 µm, 890 µm-900 µm, 900 µm-910 µm, 910 µm-920 µm, 920 µm-930 µm, 930 µm-940 µm, 940 µm-950 µm, 950 µm-960 µm, 960 µm-970 µm, 970 µm-980 µm, 980 µm-990 µm, or 990 µm-1000 µm.

In various configurations, the second filter can have a pore size of 200 µm to 600 µm. In various configurations, the second filter can have a pore size of 210 µm to 590 µm, 220 µm to 580 µm, 230 µm to 570 µm, 240 µm to 560 µm, 250 µm to 550 µm, 260 µm to 540 µm, 270 µm to 530 µm, 280 µm to 520 µm, 290 µm to 510 µm, 300 µm to 500 µm, 310 µm to 490 µm, 320 µm to 480 µm, 330 µm to 470 µm, 340 µm to 460 µm, 350 µm to 450 µm, 360 µm to 440 µm, 370 µm to 430 µm, 380 µm to 420 µm, or 390 µm to 410 µm. In various configurations, the second filter can have a pore size of 200 µm-210 µm, 210 µm-220 µm, 220 µm-230 µm, 230 µm-240 µm, 240 µm-250 µm, 250 µm-260 µm, 260 µm-270 µm, 270 µm-280 µm, 280 µm-290 µm, 290 µm-300 µm, 292 µm-302 µm, 295 µm-305 µm, 297 µm-307 µm, 300 µm-310 µm, 310 µm-320 µm, 320 µm-330 µm, 330 µm-340 µm, or 340 µm-350 µm, 350 µm-360 µm, 360 µm-370 µm, 370 µm-380 µm, 380 µm-390 µm, 390 µm-400 µm, 400 µm-410 µm, 410 µm-420 µm, 420 µm-430 µm, 430 µm-440 µm, 440 µm-450 µm, 450 µm-460 µm, 460 µm-470 µm, 470 µm-480 µm, 480 µm-490 µm, 490 µm-500 µm, 500 µm-510 µm, 510 µm-520 µm, 520 µm-530 µm, 530 µm-540 µm, 540 µm-550 µm, 550 µm-560 µm, 560 µm-570 µm, 570 µm-580 µm, 580 µm-590 µm, or 590 µm-600 µm.

In various configurations, the third filter can have a pore size of 100 µm to 300 µm. In various configurations, the third filter can have a pore size of 110 µm to 290 µm, 120 µm to 280 µm, 130 µm to 270 µm, 140 µm to 260 µm, 150 µm to 250 µm, 160 µm to 240 µm, 170 µm to 230 µm, 180 µm to 220 µm, or 190 µm to 210 µm. In various configurations, the third filter can have a pore size of 100 µm-110 µm, 110 µm-120 µm, 120 µm-130 µm, 130 µm-140 µm, 140 µm-150 µm, 145 µm-155 µm, 150 µm-160 µm, 160 µm-170 µm, 170 µm-180 µm, 180 µm-190 µm, 190 µm-200 µm, 200 µm-210 µm, 210 µm-220 µm, 220 µm-230 µm, 230 µm-240 µm, 240 µm-250 µm, 250 µm-260 µm, 260 µm-270 µm, 270 µm-280 µm, 280 µm-290 µm, 290 µm-300 µm.

The filtration apparatus 100 of FIG. 3 is an embodiment which includes a barrel, such as a syringe-like barrel 11 defining an interior space configured for containing a sample of interest, such as a LAB-containing sample of interest, e.g., into which a sample of corn mash may be poured. The syringe further comprises a plunger 12 which fits snugly but movably within the syringe barrel 11 and can be manipulated to purge, i.e., mechanically force the sample of corn mash through one or multiple filters 13 such as screen meshes sized to allow, e.g., LAB cells of interest to pass through pores in the filter(s), but to substantially screen out bulk organic matter contained in the corn mash or other LAB-containing sample of interest. In an embodiment, the filter 13 comprises the filters 1, 2, and 3. The filtration apparatus 100 as embodied herein can also be one in combination with other types of samples of interest which would benefit from the unique attributes of such apparatus 100, e.g., agriculturally-related, environmentally-related and industrially-related samples of interest; and more particularly, as applied in combination with fermentation-related and corn mash-related samples which would benefit from the apparatus's structure and function in order to enhance the user's ability to screen out bulk and other organic material and separate them from the targeted cells. The filters can be housed within or located next to a cap, or other receptacle portion 14 of the filtration apparatus 100, e.g., at one end of the syringe barrel. In an alternative to a receptacle housed within or next to the filters, the apparatus may be supplied with a cap including a conduit 14 or a conduit directly connected for transfer of the LAB-cell containing portion to such a receptacle external to the apparatus (not shown). By applying pressure to a syringe handle 15 or other such device attached or integral to the plunger for urging the sample of interest toward the filter, this filtering process serves to facilitate the removal of the excessive starch-releasing particles from the crude sample, which remain trapped behind the screen mesh or meshes 13 that otherwise can significantly inhibit the downstream detection/quantification assay. Simultaneously, the filtration allows the LAB bacterial cells to pass through the pores of the mesh or meshes 13 and be readied to undergo nucleic acid extraction. While Applicants believe that the purification and filtration methods and apparatuses provided herein for the field of quantification of LAB, especially in biological and fermentation samples such as corn mash as detailed herein are independently patentable, those skilled in the art would have knowledge of alternative purification and filtration methods which can provide alternatives which can be used with the detection and quantification of LAB methods, compositions and kits described herein with the use of various meshes or other approaches prior to extraction.

As depicted in the flow chart shown in FIG. 1, in an embodiment, various chemical and physical processes are used to produce a LAB-containing supernatant of nucleic acids from the sample filtrate. In such a nucleic acid extraction, a filtered sample volume can be added to a matrix containing a chelating agent (or other ion exchange resin) and a digestive enzyme. The resulting mixture is held constant at a specified temperature for a finite time, followed by reagent inactivation. This incubation is then followed by centrifugation. In the preferred embodiment of the method depicted in FIG. 1, the supernatant containing lysed LAB cells can for use in conducting a universal (or targeted) LAB assay. Again, one skilled in the art would have knowledge of alternative types of chelating resins, such as InstaGene Matrix™, Chelex® Extraction Solution, and/or extraction techniques utilizing sonication.

In various configurations, the filtered sample can range in volume from 20 µl to 1000 µl. In various configurations, the filtered sample volume can be from 20 µl-30 µl, 30 µl-40 µl, 40 µl-50 µl, 50 µl-60 µl, 60 µl-70 µl, 70 µl-80 µl, 80 µl-90 µl, 90 µl-100 µl, 100 µl-110 µl, 110 µl-120 µl, 120 µl-130 µl, 130 µl-140 µl, 140 µl-150 µl, 150 µl-160 µl, 160 µl-170 µl, 170 µl-180 µl, 180 µl-190 µl, 190 µl-200 µl, 210 µl-220 µl, 220 µl-230 µl, 230 µl-240 µl, 240 µl-250 µl, 250 µl-260 µl, 260 µl-270 µl, 270 µl-280 µl, 280 µl-290 µl, 290 µl-300 µl, 310

µl-320 µl, 320 µl-330 µl, 330 µl-340 µl, 340 µl-350 µl, 350 µl-360 µl, 360 µl-370 µl, 370 µl-380 µl, 380 µl-390 µl, 390 µl-400 µl, 410 µl-420 µl, 420 µl-430 µl, 430 µl-440 µl, 440 µl-450 µl, 450 µl-460 µl, 460 µl-470 µl, 470 µl-480 µl, 480 µl-490 µl, 490 µl-500 µl, 510 µl-520 µl, 520 µl-530 µl, 530 µl-540 µl, 540 µl-550 µl, 550 µl-560 µl, 560 µl-570 µl, 570 µl-580 µl, 580 µl-590 µl, 590 µl-600 µl, 610 µl-620 µl, 620 µl-630 µl, 630 µl-640 µl, 640 µl-650 µl, 650 µl-660 µl, 660 µl-670 µl, 670 µl-680 µl, 680 µl-690 µl, 690 µl-700 µl, 710 µl-720 µl, 720 µl-730 µl, 730 µl-740 µl, 740 µl-750 µl, 750 µl-760 µl, 760 µl-770 µl, 770 µl-780 µl, 780 µl-790 µl, 790 µl-800 µl, 810 µl-820 µl, 820 µl-830 µl, 830 µl-840 µl, 840 µl-850 µl, 850 µl-860 µl, 860 µl-870 µl, 870 µl-880 µl, 880 µl-890 µl, 890 µl-900 µl, 910 µl-920 µl, 920 µl-930 µl, 930 µl-940 µl, 940 µl-950 µl, 950 µl-960 µl, 960 µl-970 µl, 970 µl-980 µl, 980 µl-990 µl, or 990 µl-1000 µl.

In various configurations, a filtered sample volume can be added to a matrix containing a chelating agent (or other ion exchange resin) that can range in percentage from 5%-20%. In various configurations, the percentage can be about 5%, 6%, 7%, 8%, 9%, 10%, 11%, 12%, 13%, 14%, 15%, 16%, 17%, 18%, 19%, or 20%. In some embodiments, aliquots of the reagents are provided.

In various configurations, the matrix containing a chelating agent (or other ion exchange resin) and a digestive enzyme that ranges in concentration from 0.1-1.0 mg/ml. In various configurations, the concentration can be 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml.

In various configurations, the sample combined with the matrix is incubated at temperatures of 56-65° C. In various configurations, the temperature for incubation can be at 56° C., 57° C., 58° C., 59° C., 60° C., 61° C., 62° C., 63° C., 64° C., or 65° C.

In various configurations, the sample combined with the matrix is held at a constant temperature for a period of time ranging from 10 minutes to 30 minutes. In various configurations, the time can be 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, or 30 minutes.

In various configurations, the inactivation period can be from 5 minutes to 20 minutes. In various configurations, the inactivation period can from 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, or 20 minutes. Temperatures for conducting such inactivation sessions can be, e.g., from at least 80° C. and greater, which is generally within the knowledge of those skilled in this art.

A universal LAB assay of the invention, as presented, can be provided, e.g. as a kit containing single use tubes or in a bulk quantity in a format that contains all of the necessary components to amplify, detect and quantify, that is targeted towards particular genera and/or species of LAB, including the most common LAB contaminants found within a fermentation sample, Lactobacillus, Pediococcus and Weissella. In preferred embodiments, the universal LAB quantification kits provide the reagents and consumables needed to measure the LAB levels in most any identified substrate. This standardized approach allows for greatly increased repeatability and reproducibility of test results from less experienced users having limited to no molecular biology experience, e.g., by minimizing the number of pipetting steps required.

Included in the methods of the invention are application of the kits and methods to collect samples in and track levels of the LAB during detection and quantitative testing of laboratory, agriculturally-, environmentally- and industrially-related sampling, including every phase of a fermentation process. By using these kits and methods to detect and quantify the presence and levels of LAB following the teachings of Applicants' invention, users can, e.g., identify locations in ethanol facilities where bacterial build-up has occurred, monitor troubleshooting ventures in fermentation batches that are not doing as well as expected, monitor during decontamination efforts, and control and guide appropriate antibiotic usage based on test results.

In another embodiment of the invention, the universal LAB quantification kits and methods are integrated into automated on-demand molecular diagnostic systems such as the GeneXpert® offered commercially by Cepheid. Such automated cartridge technology, as exemplified by the GeneXpert® system, provides for inserting samples of interest into the cartridge, and through the use of sonication, completion of the nucleic acid extraction step through the quantitative PCR analysis step as otherwise outlined in FIG. 1, in an automated manner.

The assay components may include at least the real-time qPCR oligonucleotide probes and forward and reverse primers configured for such LAB targets as found within at least, but not limited to, over thirty species of Lactobacillus, Pediococcus and Weissella, and in various combinations. See, e.g., Table 1, below. Applicants have discovered that the nucleotides encoding the 16S rRNA gene from Lactobacillus delbrueckii subsp. delbrueckii strain NBRC 3202 (Accession number: NZ_BEWJ01000039.1, whole genome 12,774 bp obtained from GenBank) starting at base pair 8,420 through 8,845, were viable to be used to extract the corresponding gene region from all other Lactobacillus, Pediococcus and Weissella species previously identified in corn-based fuel fermentations (Table 1) (Chang et al. 1995; Skinner and Leathers, 2004; Lucena et al. 2010). Upon analysis, Applicants further discovered that this particular sequence has from 1-6 copies per genome, depending upon strain, which can be taken into consideration when extrapolating quantities.

TABLE 1

Lactic acid bacterial species specifically detected by the preferred primers and probe sets as detailed in Table 2.

| Lactic Acid Bacterial Species | SEQ ID NO: 4 Probe | SEQ ID NO: 9 Probe |
|---|---|---|
| Lactobacillus acidophilus | ✓ | |
| Lactobacillus amylovorus | ✓ | |
| Lactobacillus brevis | ✓ | |
| Lactobacillus buchneri | ✓ | |
| Lactobacillus casei | ✓ | |
| Lactobacillus crispatus | ✓ | |
| Lactobacillus delbrueckii | ✓ | |
| Lactobacillus delbrueckii subsp. delbrueckii | ✓ | |
| Lactobacillus delbrueckii subsp. lactis | ✓ | |
| Lactobacillus diolivorans-like | ✓ | |
| Lactobacillus ferintoshensis (aka parabuchneri) | ✓ | |
| Lactobacillus fermentum | | ✓ |
| Lactobacillus gasseri | | ✓ |
| Lactobacillus helveticus | | ✓ |
| Lactobacillus hilgardii | | ✓ |
| Lactobacillus lindneri | | ✓ |
| Lactobacillus manihotivorans | | ✓ |
| Lactobacillus mucosae | | ✓ |

TABLE 1-continued

Lactic acid bacterial species specifically detected by the
preferred primers and probe sets as detailed in Table 2.

| Lactic Acid Bacterial Species | SEQ ID NO: 4 Probe | SEQ ID NO: 9 Probe |
|---|---|---|
| *Lactobacillus nagelii* | ✓ | |
| *Lactobacillus paracasei* subsp. *paracasei* | ✓ | |
| *Lactobacillus pentosus* | ✓ | |
| *Lactobacillus plantarum* | ✓ | |
| *Lactobacillus reuteri* | ✓ | |
| *Lactobacillus rhamnosus* | ✓ | |
| *Lactobacillus salivarius* subsp. *salivarius* | ✓ | |
| *Lactobacillus vini* | ✓ | |
| *Pediococcus acidilactici* | ✓ | |
| *Pediococcus damnosus* | ✓ | |
| *Pediococcus inopinatus* | ✓ | |
| *Pediococcus parvulus* | ✓ | |
| *Pediococcus pentosaceus* | ✓ | |
| *Weissella confuse* | | ✓ |
| *Weissella paramesenteroides* | | ✓ |
| *Weissella viridescens* | | ✓ |
| *Dekkera bruxellensis* (aka *abstinens*) | No significant similarity found | |
| *Saccharomyces cerevisiae* | No significant similarity found | |

Non-limiting examples of sequences of oligonucleotide primers and probes of the present teachings are set forth in Table 2.

TABLE 2

The nucleotide sequences for preferred primers and probe sets.

| Set | Forward Primer (5'-3') | Probe (5'-3') | Reverse Primer (5'-3') | Product Size (bp) |
|---|---|---|---|---|
| 1 | GGAGGCAGCAGTAGG GAATC (SEQ ID NO: 1) | TGAAGAAGGGT TTCGGCTCG (SEQ ID NO: 2) | TGCCACCTACGTATTA CCGC (SEQ ID NO: 3) | 200 |
| 2 | GCGGTAATACGTAGGT GGCA (SEQ ID NO: 4) | TGTCCGGATTTA TTGGGCGT (SEQ ID NO: 5) | ACCGCTACACATGGA GTTCC (SEQ ID NO: 6) | 166 |
| 3 | GGAGGCAGCAGTAGG GAATC (SEQ ID NO: 1) | TGAAGAAGGGT TTCGGCTCG (SEQ ID NO: 2) | ACGCTTGCCACCTAC GTATT (SEQ ID NO: 7) | 305 |
| 4 | GGAGGCAGCAGTAGG GAATC (SEQ ID NO: 1) | TGAAGAAGGGT TTCGGCTCG (SEQ ID NO: 2) | AACGCTTGCCACCTA CGTAT (SEQ ID NO: 8) | 206 |
| 5 | GGAGGCAGCAGTAGG GAATC (SEQ ID NO: 1) | GCGGTAATACG TAGGTGGCA (SEQ ID NO: 4) | ACCGCTACACATGGA GTTCC (SEQ ID NO: 6) | 346 |
| 6 | GGAGGCAGCAGTAGG GAATC (SEQ ID NO: 1) | GCGGTAATACG TATGTTCCA (SEQ ID NO: 9) | ACCGCTACACATGGA GTTCC (SEQ ID NO: 6) | 346 |

The LAB kits and assays of the invention can be used in various combinations. For example, they can be targeted to detect simultaneously all genera targets, only the *Lactobacillus* and *Pediococcus* targets, or just the *Weissella* target, in a single tube by specific selection of primers and probes. Thus, particular kits would allow for the detection of all three genera simultaneously (*Weissella, Pediococcus* and *Lactobacillus*), only two targets (*Pediococcus* and *Lactobacillus*), or just one target (*Weissella*). SEQ ID NO: 4 detects both *Pediococcus* and *Lactobacillus*. SEQ ID NO: 9 detects only *Weissella* species. As known by those skilled in the art, workable close sequence identity of alternative forward, reverse primers and probes, e.g., of those listed in Table 2 above, such as those within the range of 70%-99.9% sequence similarity, within 5 bps-50 bps of sequence length, and/or including additions and deletions to such sequences, and any modification made by sliding or shifting the sequences by a few nucleotides, may be designed or discovered and tested, given the teachings of this invention. Such workable alternative primers and probes, together with those that use any degenerate or alternative bases for making any of the primers and probes as set forth in Table 2, or the modified primers outlined above are also within the scope of the present invention.

In various embodiments, a qPCR probe of the present teachings can comprise, consist essentially of, or consist of a DNA oligonucleotide, a fluorophore, and at least one quencher, wherein the DNA oligonucleotide can consist of a sequence selected from the group consisting of TGAAGAAGGGTTTCGGCTCG (SEQ ID NO: 2), GCGGTAATACGTAGGTGGCA (SEQ ID NO: 4), TGTCCGGATTTATTGGGCGT (SEQ ID NO: 5), and GCGGTAATACGTATGTTCCA (SEQ ID NO: 9). In various configurations, the at least one quencher can be two quenchers, such as, for example, a combination of a Zen quencher and an Iowa Black quencher as described in Xia, H. et al., BioTechniques 60: 28-34, 2016.

In various configurations, the sequence of an oligonucleotide primer or probe can have at least 70%, at least 75%, at least 80%, at least 85%, at least 90%, at least 95%, or 100% sequence identity with a primer or probe described herein, e.g., a sequence can have at least 14, at least 15, at least 16, at least 17, at least 18 bases, at least 19 bases, or all bases identical to the sequence of a primer or probe set forth herein.

In various embodiments, a composition of the present teachings can comprise, consist of, or consist essentially of i) a qPCR probe consisting of an oligonucleotide, a fluorophore and at least one quencher, wherein the probe hybridizes under stringent conditions to *Lactobacillus* bacteria of species not limited to *L. acidophilus, L. amylovorus, L. brevis, L. buchneri, L. casei, L. crispatus, L. delbrueckii* subsp. *delbrueckii, L. delbrueckii* subsp. *lactis, L. dioliv-orans*-like, *L. ferintoshensis* (aka *parabuchneri*), *L. fermen-tum, L. gasseri, L. helveticus, L. hilgardii, L. lindneri, L. manihotivorans, L. mucosae, L. nagelii, L. paracasei* subsp. *paracasei, L. pentosus, L. plantarum, L. reuteri, L. rham-nosus, L. salivarius* subsp. *salivarius* and *L. vini*; ii) a first oligonucleotide primer which can hybridize under stringent conditions to the *Lactobacillus* bacteria species; and iii) a second oligonucleotide primer which can hybridize under stringent conditions to the *Lactobacillus* bacteria species. In various configurations, the at least one quencher can be two quenchers. In various configurations, each of the probe, the first oligonucleotide primer and the second oligonucleotide primer can hybridize to a complementary sequence within the 16S rRNA gene. In various configurations, each of the first oligonucleotide primer and the second oligonucleotide primer can be, independently, from 15 bases to 25 bases in length. In various configurations, a probe can be from 5 bases to 25 bases in length, and can further include a fluorophore and quencher(s). In various configurations, each of the probe, the first oligonucleotide primer, and the second oligonucleotide primer can be 20 bases in length. In various configurations, each of the probe, the first oligonucleotide primer, and the second oligonucleotide primer can be 18 bases in length. In various configurations, each of the first oligonucleotide primer, and the second oligonucleotide primer can independently comprise, consist essentially of, or consist of 15 bases, 16 bases, 17 bases, 18 bases, 19 bases, 20 bases, 21 bases, 22 bases, 23 bases, 24 bases or 25 bases. In various configurations, the probe can comprise, consist essentially of, or consist of one, two or more fluorophores, one, two or more quenchers, and 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases or 25 bases.

In various embodiments, a composition of the present teachings can comprise, consist of, or consist essentially of i) a qPCR probe consisting of an oligonucleotide, a fluorophore and at least one quencher, wherein the probe hybridizes under stringent conditions to *Pediococcus* bacteria of species not limited to *P. acidilactici, P. damnosus, P. inopi-natus, P. parvulus,* and *P. pentosaceus*; ii) a first oligonucle-otide primer which can hybridize under stringent conditions to the *Pediococcus* bacteria species; and iii) a second oligonucleotide primer which can hybridize under stringent conditions to the *Pediococcus* bacteria species. In various configurations, the at least one quencher can be two quench-ers. In various configurations, each of the probe, the first oligonucleotide primer and the second oligonucleotide primer can hybridize to a complementary sequence within the 16S rRNA gene. In various configurations, each of the first oligonucleotide primer and the second oligonucleotide primer can be, independently, from 15 bases to 25 bases in length. In various configurations, a probe can be from 5 bases to 25 bases in length, and can further include a fluorophore and quencher(s). In various configurations, each of the probe, the first oligonucleotide primer, and the second oligonucleotide primer can be 20 bases in length. In various configurations, each of the probe, the first oligonucleotide primer, and the second oligonucleotide primer can be 18 bases in length. In various configurations, each of the first oligonucleotide primer, and the second oligonucleotide primer can independently comprise, consist essentially of, or consist of 15 bases, 16 bases, 17 bases, 18 bases, 19 bases, 20 bases, 21 bases, 22 bases, 23 bases, 24 bases or 25 bases. In various configurations, the probe can comprise, consist essentially of, or consist of one, two or more fluorophores, one, two or more quenchers, and 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases or 25 bases.

In various embodiments, a composition of the present teachings can comprise, consist of, or consist essentially of i) a qPCR probe consisting of an oligonucleotide, a fluorophore and at least one quencher, wherein the probe hybridizes under stringent conditions to *Weissella* bacteria of species not limited to *W. confusa, W. paramesenteroides,* and *W. viridescens*; ii) a first oligonucleotide primer which can hybridize under stringent conditions to the *Weissella* bacte-ria species; and iii) a second oligonucleotide primer which can hybridize under stringent conditions to the *Weissella* bacteria species. In various configurations, the at least one quencher can be two quenchers. In various configurations, each of the probe, the first oligonucleotide primer and the second oligonucleotide primer can hybridize to a comple-mentary sequence within the 16S rRNA gene. In various configurations, each of the first oligonucleotide primer and the second oligonucleotide primer can be, independently, from 15 bases to 25 bases in length. In various configura-tions, a probe can be from 5 bases to 25 bases in length, and can further include a fluorophore and quencher(s). In various configurations, each of the probe, the first oligonucleotide primer, and the second oligonucleotide primer can be 20 bases in length. In various configurations, each of the probe, the first oligonucleotide primer, and the second oligonucle-otide primer can be 18 bases in length. In various configu-rations, each of the first oligonucleotide primer, and the second oligonucleotide primer can independently comprise, consist essentially of, or consist of 15 bases, 16 bases, 17 bases, 18 bases, 19 bases, 20 bases, 21 bases, 22 bases, 23 bases, 24 bases or 25 bases. In various configurations, the probe can comprise, consist essentially of, or consist of one, two or more fluorophores, one, two or more quenchers, and 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 21 bases, 22 bases, 23 bases, 24 bases or 25 bases.

In various embodiments, a composition of the present teachings can comprise: i) a qPCR probe comprising, con-sisting of, or consisting essentially of a DNA oligonucle-otide, a fluorophore, and at least one quencher, wherein the DNA oligonucleotide consists of a sequence selected from the group consisting of TGAAGAAGGGTTTCGGCTCG (SEQ ID NO: 2), GCGGTAATACGTAGGTGGCA (SEQ ID NO: 4), TGTCCGGATTTA TTGGGCGT (SEQ ID NO: 5) and GCGGTAATACGTATGTTCCA (SEQ ID NO: 9); ii) a first oligonucleotide primer having a sequence selected from the group consisting of GGAGGCAGCAGTAGGGAATC (SEQ ID NO: 1) and GCGGTAATACGTAGGTGGCA (SEQ ID NO: 4), and iii) a second oligonucleotide primer having a sequence selected from the group consisting of TGCCACCTACGTATTACCGC (SEQ ID NO: 3), ACCGC-TACACATGGAGTTCC (SEQ ID NO: 6), ACGCTTGC-CACCTACGTATT (SEQ ID NO: 7), and AACGCTTGC-CACCTACGTAT (SEQ ID NO: 8). In various configurations, the at least one quencher can be two quench-ers. In various configurations, the sequence of the qPCR probe can be TGAAGAAGGGTTTCGGCTCG (SEQ ID NO: 2), the sequence of the first oligonucleotide primer can be GGAGGCAGCAGTAGGGAATC (SEQ ID NO: 1), and the sequence of the second oligonucleotide primer can be TGCCACCTACGTATTACCGC (SEQ ID NO: 3). In various configurations, the sequence of the qPCR probe can be TGTCCGGATTTATTGGGCGT (SEQ ID NO: 5), the sequence of the first PCR primer can be GCGGTAATACGTAGGTGGCA (SEQ ID NO: 4), and the sequence of the second PCR primer can be ACCGCTACA-CATGGAGTTCC (SEQ ID NO: 6). In various configurations, the sequence of the qPCR probe can be TGAAGAAGGGTTTCGGCTCG (SEQ ID NO: 2), the sequence of the first PCR primer can be GGAGGCAGCAGTAGGGAATC (SEQ ID NO: 1), and the sequence of the second PCR primer can be ACGCTTGC-CACCTACGTATT (SEQ ID NO: 7). In various configurations, the sequence of the qPCR probe can be TGAAGAAGGGTTTCGGCTCG (SEQ ID NO: 2), the sequence of the first PCR primer can be GGAGGCAGCAGTAGGGAATC (SEQ ID NO: 1), and the sequence of the second PCR primer can be AACGCTTGC-CACCTACGTAT (SEQ ID NO: 8). In various configurations, the sequence of the qPCR probe can be GCGGTAATACGTAGGTGGCA (SEQ ID NO: 4), the sequence of the first PCR primer can be GGAGGCAGCAGTAGGGAATC (SEQ ID NO: 1), and the sequence of the second PCR primer can be ACCGCTACA-CATGGAGTTCC (SEQ ID NO: 6). In various configurations, the sequence of the qPCR probe can be GCGGTAATACGTATGTTCCA (SEQ ID NO: 9), the sequence of the first PCR primer can be GGAGGCAGCAGTAGGGAATC (SEQ ID NO: 1), and the sequence of the second PCR primer can be ACCGCTACA-CATGGAGTTCC (SEQ ID NO: 6).

In various configurations, a composition in accordance with the present teachings can further comprise a plurality of dNTPs and a DNA polymerase.

In various embodiments, the present teachings include a kit comprising a qPCR probe comprising, consisting of, or consisting essentially of, a DNA oligonucleotide, a fluorophore, and at least one quencher, wherein the DNA oligonucleotide consists of a sequence selected from the group consisting of TGAAGAAGGGTTTCGGCTCG (SEQ ID NO: 2), GCGGTAATACGTAGGTGGCA (SEQ ID NO: 4), TGTCCGGATTTATTGGGCGT (SEQ ID NO: 5) and GCGGTAATACGTATGTTCCA (SEQ ID NO: 9); ii) a first oligonucleotide primer having a sequence selected from the group consisting of GGAGGCAGCAGTAGGGAATC (SEQ ID NO: 1) and GCGGTAATACGTAGGTGGCA (SEQ ID NO: 4); and iii) a second oligonucleotide primer having a sequence selected from the group consisting of TGCCACCTACGTATTACCGC (SEQ ID NO: 3), ACCGC-TACACATGGAGTTCC (SEQ ID NO: 6), ACGCTTGC-CACCTACGTATT (SEQ ID NO: 7), and AACGCTTGC-CACCTACGTAT (SEQ ID NO: 8). In some configurations, the at least one quencher can be two quenchers. In various configurations, a kit can further comprise a DNA polymerase. In some configurations, the DNA polymerase can be a thermostable DNA polymerase. In some configurations, the kit can further comprise dNTPs. In various configurations a kit can further comprise a PCR master mix.

In various embodiments, a method of quantifying lactic acid bacteria in a sample, can comprise: a) providing a sample comprising or suspected of comprising LAB bacteria; b) extracting from the sample an aqueous-soluble fraction comprising DNA; b) forming a mixture comprising the DNA and a reaction mixture comprising a qPCR probe, a first oligonucleotide primer, and a second nucleotide primer in accordance with the present teachings; and c) performing a qPCR amplification on the mixture. In some configurations, the performing a qPCR amplification comprises determining a cycle threshold (Ct) value for the sample wherein a Ct value below a cut-off value indicates the presence of LAB in the sample. In various configurations, the sample can comprise or can be, for example and without limitation, a corn mash, a cereal mash, or a cabbage mash. In some configurations, the sample can comprise a corn mash. In various configurations, the sequence of the first oligonucleotide primer can be GGAGGCAGCAGTAGGGAATC (SEQ ID NO: 1), the sequence of the second PCR primer can be TGCCACCTACGTATTACCGC (SEQ ID NO: 3), and the sequence of the qPCR probe can be TGAAGAAGGGTTTCGGCTCG (SEQ ID NO: 2). In various configurations, the sequence of the first oligonucleotide primer can be GCGGTAATACGTAGGTGGCA (SEQ ID NO: 4), the sequence of the second oligonucleotide primer can be ACCGCTACACATGGAGTTCC (SEQ ID NO: 6), and the sequence of the qPCR probe can be TGTCCGGAT-TTATTGGGCGT (SEQ ID NO: 5). In various configurations, the sequence of the first oligonucleotide primer can be GGAGGCAGCAGTAGGGAATC (SEQ ID NO: 1), the sequence of the second PCR primer can be ACGCTTGC-CACCTACGTATT (SEQ ID NO: 7), and the sequence of the qPCR probe can be TGAAGAAGGGTTTCGGCTCG (SEQ ID NO: 2). In various configurations, the sequence of the first oligonucleotide primer can be GGAGGCAGCAGTAGGGAATC (SEQ ID NO: 1), the sequence of the second PCR primer can be AACGCTTGC-CACCTACGTAT (SEQ ID NO: 8), and the sequence of the qPCR probe can be TGAAGAAGGGTTTCGGCTCG (SEQ ID NO: 2). In various configurations, the sequence of the first oligonucleotide primer can be GGAGGCAGCAGTAGGGAATC (SEQ ID NO: 1), the sequence of the second PCR primer can be ACCGCTACA-CATGGAGTTCC (SEQ ID NO: 6), and the sequence of the qPCR probe can be GCGGTAATACGTAGGTGGCA (SEQ ID NO: 4). In various configurations, the sequence of the first oligonucleotide primer can be GGAGGCAGCAGTAGGGAATC (SEQ ID NO: 1), the sequence of the second PCR primer can be ACCGCTACA-CATGGAGTTCC (SEQ ID NO: 6), and the sequence of the qPCR probe can be GCGGTAATACGTATGTTCCA (SEQ ID NO: 9).

The present inventors have developed qPCR-based assays for the detection and quantification of at least, but not limited to, over 30 different lactic acid bacterial species and as described above, of other LAB genera commonly found as contaminants of ethanol production, and other fermentation systems such as, for example, fermentations of corn mash, wheat mash, beer, and sauerkraut.

Furthermore, in addition to the presently preferred embodiment as featured in FIGS. 1 and 3, the present inventors have developed a system, including an apparatus and method, for preparing fermentation mixtures such as mash samples for use in assays for detecting LAB. The methods of the system can be used to detect LAB from any sample source, such as but not limited to corn mash undergoing fermentation, bee populations, soil, and agricultural crops. In their system, particles that are slightly larger than most bacteria can be sieved out. In their methods, a filtrate can be collected which can be subjected to molecular analysis, such as a PCR analysis, for detection of contaminating LAB. When used in conjunction with a universal LAB PCR-based assay described herein, contaminating lactic acid bacteria in a sample can be detected and quantified.

Samples of mash can be obtained at any time point during the production of ethanol and analyzed for LAB contamination.

In various configurations, a qPCR amplification can comprise cyclically heating the mixture to a denaturation temperature such as 95° C. then to a reannealing/extension temperature which can be from 60° C.-70° C., for one or more cycles. In various configurations, the reannealing/extension temperature can be, for example, 60° C., 61° C., 62° C., 63° C., 64° C., 65° C., 66° C., 67° C., 68° C., 69° C., 70° C. or a combination thereof. A mixture can be considered positive for the presence of LAB if a fluorescence signal is detected and a cycle threshold (Ct value, defined as the number of cycles required for a qPCR fluorescence signal to exceed a background level) can be determined, after 1 cycle, 2 cycles, or more cycles, in view of experimentally determined detection thresholds. In various configurations, the cyclical heating can consist of 1 cycle, 2 cycles, 3 cycles, 4 cycles 5 cycles, 6 cycles, 7 cycles, 8 cycles, 9 cycles, 10 cycles, 11 cycles, 12 cycles, 13 cycles, 14 cycles 15 cycles, 15 cycles, 16 cycles, 17 cycles, 18 cycles, 19 cycles, 20 cycles, 21 cycles, 22 cycles, 23 cycles, 24 cycles, 25 cycles, 26 cycles, 27 cycles, 28 cycles, 29 cycles, 30 cycles, 31 cycles, 32 cycles, 33 cycles, 34 cycles, 35 cycles, 36 cycles, 37 cycles, 38 cycles, 39 cycles, 40 cycles, or as many cycles as the practitioner determines. In some configurations, a fluorescence signal generated during the thermal cycling can correlate to a Ct value, which can be used to quantify the LAB comprised by a sample.

In some configurations, the PCR amplification can further comprise an initial denaturation step which can last from 30 seconds up to 15 minutes at 95° C. In some configurations, the initial denaturation step can be 30 seconds to 2 minutes. In various configurations, the initial denaturation step can be 2 minutes. In various configurations, the LAB can be selected from the group consisting but not limited to, *L. acidophilus, L. amylovorus, L. brevis, L. buchneri, L. casei, L. crispatus, L. delbrueckii* subsp. *delbrueckii, L. delbrueckii* subsp. *lactic, L. diolivorans*-like, *L. ferintoshensis* (aka *parabuchneri*), *L. fermentum, L. gasseri, L. helveticus, L. hilgardii, L. lindneri, L. manihotivorans, L. mucosae, L. nagelii, L. paracasei* subsp. *paracasei, L. pentosus, L. plantarum, L. reuteri, L. rhamnosus, L. salivarius* subsp. *salivarius, L. vini, P. acidilactici, P. damnosus, P. inopinatus, P. parvulus, P. pentosaceus, W. confusa, W. paramesenteroides,* and *W. viridescens,* and any combination thereof.

In some configurations, a method of quantifying *Lactobacillus, Pediococcus* or *Weissella* bacteria in a sample can comprise preparing a biological sample for a qPCR analysis in accordance with the present teachings; and performing a qPCR analysis on the extracted DNA. In various configurations, the performing a qPCR analysis on the extracted DNA can comprise forming a mixture comprising the extracted DNA, a probe, a first oligonucleotide primer, and a second oligonucleotide primer; subjecting the mixture to thermal cycling; detecting a fluorescence emission signal from the mixture in real time; and determining a Ct value of the thermally cycled mixture. In various configurations, standards can be used to calibrate a qPCR analysis, and a cut-off Ct value for detecting LAB can be determined. A skilled artisan will be able to determine a Ct value indicating a positive signal which may vary with different equipment and reagents. In some configurations, a Ct value of less than 30 can indicate the presence of *Lactobacillus, Pediococcus* or *Weissella* bacteria, whereas a Ct value of 30 or greater can be considered to be background or "noise." In some configurations, a Ct value of less than 32 can indicate the presence of *Lactobacillus, Pediococcus* or *Weissella* bacteria. In some configurations, a Ct value of less than 31 can indicate the presence of *Lactobacillus, Pediococcus* or *Weissella* bacteria, whereas a Ct value of 31 or greater can be considered to be background or "noise.", whereas a Ct value of 32 or greater can be considered to be background or "noise." In some configurations, a Ct value of less than 33 can indicate the presence of *Lactobacillus, Pediococcus* or *Weissella* bacteria, whereas a Ct value of 33 or greater can be considered to be background or "noise." In some configurations, a Ct value of less than 34 can indicate the presence of *Lactobacillus, Pediococcus* or *Weissella* bacteria, whereas a Ct value of 34 or greater can be considered to be background or "noise." In some configurations, a Ct value of less than 35 can indicate the presence of *Lactobacillus, Pediococcus* or *Weissella* bacteria, whereas a Ct value of 35 or greater can be considered to be background or "noise." In some configurations, a Ct value of less than 36 can indicate the presence of *Lactobacillus, Pediococcus* or *Weissella* bacteria, whereas a Ct value of 36 or greater can be considered to be background or "noise." In some configurations, a Ct value of less than 37 can indicate the presence of *Lactobacillus, Pediococcus* or *Weissella* bacteria, whereas a Ct value of 37 or greater can be considered to be background or "noise." In some configurations, a Ct value of less than 38 can indicate the presence of *Lactobacillus, Pediococcus* or *Weissella* bacteria, whereas a Ct value of 38 or greater can be considered to be background or "noise." In some configurations, a Ct value of less than 39 can indicate the presence of *Lactobacillus, Pediococcus* or *Weissella* bacteria, whereas a Ct value of 39 or greater can be considered to be background or "noise." In some configurations, a Ct value of less than 40 can indicate the presence of *Lactobacillus, Pediococcus* or *Weissella* bacteria, whereas a Ct value of 40 or greater can be considered to be background or "noise." In some configurations, a Ct value of less than 41 can indicate the presence of *Lactobacillus, Pediococcus* or *Weissella* bacteria, whereas a Ct value of 41 or greater can be considered to be background or "noise." In some configurations, a Ct value of less than 42 can indicate the presence of *Lactobacillus, Pediococcus* or *Weissella* bacteria, whereas a Ct value of 42 or greater can be considered to be background or "noise." In some configurations, a Ct value of less than 43 can indicate the presence of *Lactobacillus, Pediococcus* or *Weissella* bacteria, whereas a Ct value of 43 or greater can be considered to be background or "noise." In some configurations, a Ct value of less than 44 can indicate the presence of *Lactobacillus, Pediococcus* or *Weissella* bacteria, whereas a Ct value of 44 or greater can be considered to be background or "noise." In some configurations, a Ct value of less than 45 can indicate the presence of *Lactobacillus, Pediococcus* or *Weissella* bacteria, whereas a Ct value of 45 or greater can be considered to be background or "noise." In some configurations, a Ct value of less than 46 can indicate the presence of *Lactobacillus, Pediococcus* or *Weissella* bacteria, whereas a Ct value of 46 or greater can be considered to be background or "noise." In some configurations, a Ct value of less than 47 can indicate the presence of *Lactobacillus, Pediococcus* or *Weissella* bacteria, whereas a Ct value of 47 or greater can be considered to be background or "noise." In some configurations, a Ct value of less than 48 can indicate the presence of *Lactobacillus, Pediococcus* or *Weissella* bacteria, whereas a Ct value of 48 or greater can be considered to be background or "noise." In some configurations, a Ct value of less than 49 can indicate the presence of *Lactobacillus, Pediococcus* or *Weissella* bacteria, whereas a Ct value of 49 or greater can be considered to be background or "noise." In some configurations, a Ct value of less than 50 can indicate the presence of *Lactobacillus*, *Pediococcus* or *Weissella* bacteria, whereas a Ct value of 50 or greater can be considered to be background or "noise."

In various configurations, *Lactobacillus* species which can be detected by the disclosed assays can be selected from the group consisting of but not limited to *L. acidophilus*, *L. amylovorus*, *L. brevis*, *L. buchneri*, *L. casei*, *L. crispatus*, *L. delbrueckii* subsp. *delbrueckii*, *L. delbrueckii* subsp. *lactis*, *L. diolivorans*-like, *L. ferintoshensis* (aka *parabuchneri*), *L. fermentum*, *L. gasseri*, *L. helveticus*, *L. hilgardii*, *L. lindneri*, *L. manihotivorans*, *L. mucosae*, *L. nagelii*, *L. paracasei* subsp. *paracasei*, *L. pentosus*, *L. plantarum*, *L. reuteri*, *L. rhamnosus*, *L. salivarius* subsp. *salivarius*, *L. vini* and any combination thereof. In various configurations, *Pediococcus* species which can be detected by the disclosed assays can be selected from the group consisting of but not limited to *P. acidilactici*, *P. damnosus*, *P. inopinatus*, *P. parvulus*, and *P. pentosaceus* and any combination thereof. In various configurations, *Weissella* species which can be detected by the disclosed assays can be selected from the group consisting of but not limited to *W. confusa*, *W. paramesenteroides*, and *W. viridescens* and any combination thereof. In various configurations, the first oligonucleotide primer can have a sequence selected from the group consisting of GGAGGCAGCAGTAGGGAATC (SEQ ID NO: 1) and GCGGTAATACGTAGGTGGCA (SEQ ID NO: 4), the second oligonucleotide primer can have a sequence selected from the group consisting of TGCCACCTACGTAT-TACCGC (SEQ ID NO: 3), ACCGCTACACATG-GAGTTCC (SEQ ID NO: 6), ACGCTTGCCACCTACGT-ATT (SEQ ID NO: 7), and AACGCTTGCCACCTACGTAT (SEQ ID NO: 8), and the probe can have a sequence selected from the group consisting of TGAAGAAGGGTTTCGGCTCG (SEQ ID NO: 2), GCGGTAATACGTAGGTGGCA (SEQ ID NO: 4), TGTCCGGATTTATTGGGCGT (SEQ ID NO: 5), and GCGGTAATACGTATGTTCCA (SEQ ID NO: 9), wherein the probe further comprises a fluorophore and a quencher.

In various configurations, a qPCR assay can comprise forming a mixture comprising a resuspended pellet as described supra or a portion thereof, a qPCR probe, a first primer, a second primer, dNTPs and a thermostable DNA polymerase; subjecting the mixture to thermal cycling for up to 50 cycles of heating at, e.g., 95° C. for 15 seconds and heating at 60° C. for 1 minute. In various configurations, the thermal cycling can be preceded by heat at about 95° C. for 30 seconds to 15 minutes. In various configurations, the biological mixture can be or can comprise a corn mash, such as a corn mash from a corn-to-ethanol production line.

In various embodiments, the present teachings include a kit. In various configurations, a kit of the present teachings can comprise one or combinations of: i) a first oligonucleotide primer; ii) a second oligonucleotide primer; and iii) a qPCR probe in accordance with the present teachings. In various configurations, the kit can further comprise iv) a plurality of dNTPs; and v) a thermostable DNA polymerase. In various configurations, a qPCR probe can have a sequence selected from the group consisting of TGAAGAAGGGTTTCGGCTCG (SEQ ID NO: 2), GCGGTAATACGTAGGTGGCA (SEQ ID NO: 4), TGTCCGGATTTATTGGGCGT (SEQ ID NO: 5), and GCGGTAATACGTATGTTCCA (SEQ ID NO: 9). In various configurations, a first oligonucleotide primer can have a sequence selected from the group consisting of GGAGGCAGCAGTAGGGAATC (SEQ ID NO: 1), and GCGGTAATACGTAGGTGGCA (SEQ ID NO: 4). In various configurations, a second oligonucleotide primer can have a sequence selected from the group consisting of TGCCACCTACGTATTACCGC (SEQ ID NO: 3), ACCGC-TACACATGGAGTTCC (SEQ ID NO: 6), ACGCTTGC-CACCTACGTATT (SEQ ID NO: 7), and AACGCTTGC-CACCTACGTAT (SEQ ID NO: 8).

As used herein, a qPCR probe can be a DNA oligonucleotide of 15-30 nucleotide bases, and further comprises a fluorophore and at least one quencher. In various configurations, a qPCR probe can have 15-25 bases. In various configurations, a qPCR probe can have a sequence of 15-20 bases. In various configurations, a qPCR probe can have a sequence of 15, 16, 17, 18, 19, 20, 21, 22, 23, 24, 25, 26, 27, 28, 29, or 30 nucleotide bases, plus a fluorophore and at least one quencher. In various configurations, the fluorophore can be, for example and without limitation, 6-FAM (6-Carboxyfluorescein), TET™ (Tetrachlorofluorescein), JOE™ (6-carboxy-4',5'-dichloro-2',7'-dimethoxyfluorescein), YAKIMA YELLOW® (Elitech Group), VIC® (Applied Biosystems, Inc.), PET® (Applied Biosystems, Inc.), fluorescein, a rhodamine (such as tetramethylrhodamine (TAMRA™) (NHS ester), RHODAMINE RED™-X (NHS Ester), RHODAMINE GREEN™ (Carboxyrhodamine 110), ROX™ (glycine conjugate of 5-carboxy-X-rhodamine, succinimidyl ester, NHS Ester), an ATTO™ (ATTO-TEC GmbH) dye such as ATTO™ 488 (NHS Ester), ATTO™ 532 (NHS Ester), ATTO™ 550 (NHS Ester, novel fluorescent label related to the well-known dyes Rhodamine 6G and Rhodamine B), ATTO™ 565 (NHS Ester), ATTO™ 590 (NHS Ester), ATTO™ 633 (NHS Ester), ATTO™ 647N (NHS Ester, fluorescent dye for the red spectral region), ATTO™ Rhol0l, (NHS Ester, a derivative of the well-known dye Rhodamine 101), an ALEXA FLUOR® (Life Technologies) such as ALEXA FLUOR® 488 (NHS Ester), ALEXA FLUOR® 532 (NHS Ester, 1H-Pyrano[3,2-f:5,6-f]diindole-10,12-disulfonic acid, 5-[4-[[(2,5-dioxo-1-pyrrolidinyl)oxy]carbonyl]phenyl]-2,3,7,8-tetrahydro-2,3,3,7,7,8-hexamethyl-271795-14-3), ALEXA FLUOR® 546 (NHS Ester), a coumarin, CASCADE BLUE® (Life Technologies), a BODIPY® (any of several fluorescent dyes comprising a core structure 4,4-difluoro-4-bora-3a,4a-diaza-s-indacene, Life Technologies), TEXAS RED® (Life Technologies), TEX™ 615 (NHS Ester, red fluorescent dye, Integrated DNA Technologies), HEX™ (Applied Biosystems, Inc.; Hexachlorofluorescein), IRDYE® 800CW (NHS Ester) (LI-COR Biosciences), a MAXI™ NHS ester (fluorescent dye, excited with a 488 nm laser, Integrated DNA Technologies), TYE™ 563 (bright fluorescent dye, Integrated DNA Technologies), ALEXA FLUOR® 594 (NHS Ester, Pyrano[3,2-g:5,6-g']diquinolin-13-ium, 6-[2-carboxy-4(or 5)-[[(2,5-dioxo-1-pyrrolidinyl)oxy]carbonyl]phenyl]-1,2,10,11-tetrahydro-1,2,2,10,10,ll-hexamethyl-4,8-bis (sulfomethyl)-), ALEXA FLUOR® 647 (NHS Ester a bright and photostable far-red dye with excitation ideally suited to the 633 nm laser line), ALEXA FLUOR® 660 (NHS Ester, bright and photostable far-red dye with excitation ideally suited to the 633 or 647 nm laser line), TYE™ 665 (bright, fluorescent dye, Integrated DNA Technologies), TYE™ 705 (bright, fluorescent dye, Integrated DNA Technologies), ALEXA FLUOR® 750 (NHS Ester, bright and photostable near-IR dye), Lucifer Yellow, and an indocyanine (CY3™, CY5™, CY5.5™, GE Healthcare). Other commercially available fluorophores are also suitable for the present teachings.

Non-limiting examples of suitable quencher molecules include ZEN-IOWA BLACK® FQ (dark quencher, Integrated DNA Technologies), IOWA BLACK® RQ (dark quencher, Integrated DNA Technologies), TAO-IOWA BLACK® RQ, TAMRA™, QSY® 7 succinimidyl ester (Xanthylium, 9-[2-[[4-[[(2,5-dioxo-1-pyrrolidinyl)oxy]carbonyl]-1-piperidinyl]sulfonyl]phenyl]-3,6-bis(methylphenylamino)-, chloride 304014-12-8, Life Technologies), QSY® 9 succinimidyl ester (Life Technologies), QSY® 21 succinimidyl ester, (Life Technologies), QSY® 35 acetic acid, succinimidyl ester (Life Technologies), DABCYL (4-((4-(dimethylamino)phenyl)azo)benzoic acid, succinimidyl ester), dinitrophenyl (DNP), DDQ-I (Eurogentec proprietary non-fluorescent molecule quenching lower wavelength dyes), DDQ-II (Eurogentec proprietary non-fluorescent quencher with an absorbance between 550-750 nm), ECLIPSE™ (4-N-methyl-N-(4'-nitro-2'-chloroazobenzen-4-yl)-aminobutanamido-1-(2-O-dimethoxytrityloxymethyl)-pyrrolidin-4-yl-succinoyl long chain alkylamino-CPG, Epoch Biosciences), IOWA BLACK® FQ (Quencher with absorbance spectra from 420-620 nm, Integrated DNA Technologies), BHQ-1 (Biosearch Technologies) and BHQ-3 (Biosearch Technologies). Those skilled in the art can readily substitute a variety of detectable labels that can be used on the probes, selected among, but not limited to, fluorophores, radiolabels, haptens (e.g., biotin), chromogens or quenchers.

In some configurations, PCR can be carried out wherein the final concentration of the first and second oligonucleotide primer can be from 0.1 µM to 1 µM. In various configurations, the concentration of each of a forward and a reverse primer can be 0.1 µM, 0.2 µM, 0.3 µM, 0.4 µM, 0.5 µM, 0.6 µM, 0.7 µM, 0.8 µM, 0.9 µM, or 1 µM. In various configurations, the final concentration of a probe can be from 0.05 µM to 0.25 µM. In various configurations, the final concentration of a probe can be 0.05 µM, 0.06 µM, 0.07 µM, 0.08 µM, 0.09 µM, 0.1 µM 0.11 µM, 0.12 µM, 0.13 µM, 0.14 µM, 0.15 µM, 0.16 µM, 0.17 µM, 0.18 µM, 0.19 µM, 0.2 µM, 0.21 µM, 0.22 µM, 0.23 µM, 0.24 µM, or 0.25 µM.

In some configurations, a PCR protocol can comprise a 2 minute hold at 95° C. followed by 25-50 cycles of 95° C. for 15 seconds (denaturation) and 60° C. for 20 seconds up to 1 minute (for combined annealing and extension). In various configurations, the annealing temperature (combining both annealing and extension) can be 60° C. to 69° C. In various configurations, the annealing temperature can be 60° C., 61° C., 62° C., 63° C., 64° C., 65° C., 66° C., 67° C., 68° C., or 69° C. In various configurations, a PCR analysis can comprise up to 25 cycles, 26 cycles, 27 cycles, 28 cycles, 29 cycles, 30 cycles, 31 cycles, 32 cycles, 33 cycles, 34 cycles, 35 cycles, 36 cycles, 37 cycles, 38 cycles, 39 cycles, 40 cycles, 41 cycles, 42 cycles, 43 cycles, 44 cycles, 45 cycles, 46 cycles, 47 cycles, 48 cycles, 49 cycles, or up to 50 cycles of thermal cycling. In various configurations, a PCR analysis can comprise up to 40 cycles of thermal cycling.

For quantitative assays such as those disclosed herein, there are several steps within the procedure that can introduce error. Thus, results from test samples are almost always necessarily to a certain degree, best estimates of the precise true value, and analytical techniques known to those skilled in the art can be applied to account for such errors and assess repeatability and reproducibility. Such measures were employed under various conditions, and established at a level of confidence of approximately 95%, that for embodiments of the Universal LAB assay disclosed herein, the true quantity value is likely to fall within no greater than +/−2.74% of the reported quantity value. Accordingly, using the methods, kits and compositions as disclosed herein in various embodiments, reported quantitative amounts are herein provided which can reproducibly be calculated within at least +/−25%, within +/−20%, within +/−15%, within +/−12%, within +/−10, within +/−9%, within +/−8%, within +/−7%, within +/−6%, within +/−5%, within +/−4%, within +/−3%, and within +/−2.74%, and at higher quantitative percentages of true values, and are considered within the scope of the invention.

All publications cited are herein incorporated by reference, each in its entirety.

EXAMPLES

The present teachings including descriptions provided in the Examples are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1: Detection of LAB from a Variety of Sources

This example illustrates detection of LAB from a variety of sources using methods of the present teachings.

In these experiments, DNA from laboratory, agriculturally and environmentally-related samples (including food- and crop-related) were screened in duplicate using an assay of the present teachings. The sample sources are listed in Table 5. The reaction conditions were as described in Tables 3 and 4.

TABLE 5

| Samples analyzed by assays of the present teachings. | | | |
|---|---|---|---|
| Sample Name | Type | Ct Value* | Result |
| Acute Bee Paralysis Virus sDNA in bee | Bee or bee pathogen | 24.629 | Pos |
| Barley | Crop | 31.842 | Pos |
| Black Queen Cell Virus sDNA in water | Bee or bee pathogen | Und | Neg |
| Canola | Crop | 34.894 | Neg |
| *Cercospora zea maydis* | Pure culture | 37.165 | Neg |
| Chickpea | Crop | 34.840 | Neg |
| Chronic Bee Paralysis Virus sDNA in bee** | Bee or bee pathogen | 23.311 | Pos |
| *Clavibacter michiganensis* spp. *nebraskensis* | Pure culture | 31.156 | Pos |
| Corn | Crop | 34.797 | Neg |
| Deformed Wing Virus sDNA in water** | Bee or bee pathogen | Und | Neg |
| *Dekkera bruxellensis* | Pure culture | 37.173 | Neg |
| *Fusarium graminearum* | Pure culture | 36.967 | Neg |
| *Fusarium subglutinans* | Pure culture | 39.073 | Neg |
| *Fusarium verticillioides* | Pure culture | 38.203 | Neg |
| Honey bee | Bee or bee pathogen | 23.051 | Pos |
| Human | Misc. DNA | 25.016 | Pos |
| Israeli Acute Bee Paralysis Virus sDNA in water** | Bee or bee pathogen | Und | Neg |
| Kashmir Bee Virus sDNA in bee** | Bee or bee pathogen | 23.403 | Pos |
| *Lactobacillus acidophilus* | Pure culture | 16.534 | Pos |
| *Lactobacillus casei* | Pure culture | 17.962 | Pos |
| *Lactobacillus delbrueckii* | Pure culture | 16.885 | Pos |

TABLE 5-continued

Samples analyzed by assays of the present teachings.

| Sample Name | Type | Ct Value* | Result |
|---|---|---|---|
| *Lactobacillus delbrueckii lactis* | Pure culture | 22.608 | Pos |
| *Lactobacillus fermentum* | Pure culture | 18.207 | Pos |
| *Lactobacillus rhamnosus* | Pure culture | 19.519 | Pos |
| Lake Sinai Virus Type 1 and 2 sDNA in water** | Bee or bee pathogen | Und | Neg |
| Lentil | Crop | 33.896 | Neg |
| *Melissococcus plutonius* | Pure culture | 24.190 | |
| *Paenibacillus larvae* | Pure culture | Und | Neg |
| Pea | Crop | 35.221 | Neg |
| *Phytophthora sojae* | Pure culture | 24.427 | Pos |
| Rice | Crop | 35.241 | Neg |
| Salmon sperm DNA | Misc. DNA | Und | Neg |
| Slow Bee Paralysis Virus sDNA in water** | Bee or bee pathogen | Und | Neg |
| Soil - black dirt | Soil | 23.643 | Pos |
| Soil - clay | Soil | 25.804 | Pos |
| Soil - potting | Soil | 25.003 | Pos |
| Soil - sandy loam | Soil | 25.216 | Pos |
| Soybean | Crop | 39.512 | Neg |
| Spinach | Crop | 32.807 | Pos |
| Sugar beet | Crop | Und | Neg |
| Wheat | Crop | 38.518 | Neg |
| White-tailed deer | Misc. DNA | 23.730 | Pos |
| *Xanthomonas vasicola* pv. *vasculorum* | Pure culture | Und | Neg |

*"Und" = Undetermined, indicating that fluorescence signal was below the detection limit of the instrumentation throughout the thermal cycling.
**Target is sDNA of a pathogenic RNA virus.

For each sample tested (seed, soil, pure culture, etc.), as listed in Table 5, the Ct value and corresponding result are indicated. These data illustrate the ability of the disclosed methods to detect LAB in a variety of sample sources. Since the honey bee itself was found to contain a relatively high level of LAB (Ct of 23.051) most likely from the microflora within the gut, any synthetic DNA (sDNA) sample diluted with the honey bee nucleic acid would be expected to have a similar level of LAB, as opposed to those diluted in molecular water. Furthermore, *Lactobacillus* is known to be a common soil inhabitant and thus was found in all of the soil samples tested.

Example 2: The Extraction, Detection and Quantification of *Lactobacillus* DNA from Samples of Corn Mash This example, together with Example 3, illustrates the extraction, detection, and quantification of *Lactobacillus* DNA from industrially-related sources, which can include chemical processing-related, pharmaceutical-processing-related samples, such as fermentation-generated samples, e.g., of corn mash.

In these experiments, ethanol production plant samples from a batch fermentation were collected from each step along the production line starting with the water and finishing with the beer wells and the stillage that eventually provide the distillers' dried grains. After collection, samples were stored at 4° C. until they could be shipped to the National Agricultural Genotyping Center at 1605 Albrecht Blvd N Fargo, N. Dak. 58102. Each bulk sample (total of 27 samples as listed in Table 6) was processed using two different methods: a Traditional Sample Prep (TSP) Method, or a Filtering Method of the present teachings.

In the TSP method, each sample was mixed to resuspend any sedimented material. Due to the extreme viscosity of the sample material, the tip of a 1 ml pipet tip had to be cut off to allow the thick slurry to be pipetted. A volume of the slurry was transferred to a 2 ml tube. Each sample was centrifuged at low speed to allow large chunks to settle, leaving behind a liquid that could be easily and accurately pipetted. The resultant supernatant was transferred to a new 2 ml tube containing 1 glass bead and homogenized. After homogenization, the tubes were spun briefly to collect liquid before continuing with the Maxwell™ (Promega, Madison, Wis.) 96 gDNA Miniprep extraction procedure.

In a filtering method of the present teachings, the entire bulk sample was processed through a set of USA standard testing sieves (obtained from VWR (Radnor, Pa.)) as detailed in the present teachings resulting in an approximate 500 ml or less of filtered corn mash supernatant. A sample of the filtrate supernatant was removed and pelleted by centrifugation. The liquid was removed and the pellet was processed. After homogenization, the tubes were spun briefly to collect droplets before continuing with the Maxwell™ (Promega, Madison, Wis.) 96 gDNA Miniprep extraction.

The results for both sample preparation methods are summarized in Table 6. The CFU/ml values were calculated from the Ct values; CFU/ml values for *L. fermentum* were calculated from optical density readings using samples that had been homogenized (Table 6).

TABLE 6

Summarized results for samples prepared by the TSP and filtering methods.

| Sample Name | Traditional Sample Prep Method | | Filtering Method | |
|---|---|---|---|---|
| | Ct Value | LAB CFU/ml | Ct Value | LAB CFU/ml |
| Hot H₂O | 31.120 | 318,473 | 26.585 | 2,879,694 |
| Slurry | 32.902 | 97,273 | 26.823 | 2,327,601 |
| Liquefaction Tank | 33.543 | 61,037 | 29.519 | 351,928 |
| Fermentation Tank - 4 Hour | 31.758 | 211,884 | 23.070 | 34,426,540 |
| Heat Exchanger 1 out | 30.399 | 549,282 | 23.957 | 18,666,972 |
| Heat Exchanger 2 in | 32.332 | 137,671 | 27.022 | 2,130,981 |
| Heat Exchanger 2 out | 32.245 | 145,778 | 27.433 | 1,532,017 |
| Yeast Prop Start T = 0 hour | 34.814 | 25,225 | 26.723 | 2,684,560 |
| Yeast Prop Drop T = 8.5 hour | 34.620 | 57,268 | 24.708 | 11,188,297 |
| Fermentation Tank - 0 Hour | 35.508 | 16,230 | 27.025 | 2,140,711 |
| Fermentation Tank - 2 Hour | 33.600 | 59,758 | 26.109 | 3,952,171 |
| Fermentation Tank - 4 Hour | 38.505 | 1,922 | 25.788 | 4,947,406 |
| Fermentation Tank - 6 Hour | 33.079 | 80,325 | 25.308 | 7,175,860 |
| Fermentation Tank - 8 Hour | 31.911 | 185,173 | 25.094 | 8,173,550 |

TABLE 6-continued

| | Traditional Sample Prep Method | | Filtering Method | |
| Sample Name | Ct Value | LAB CFU/ml | Ct Value | LAB CFU/ml |
| --- | --- | --- | --- | --- |
| Fermentation Tank - 10 Hour | 32.514 | 122,437 | 24.821 | 10,023,610 |
| Fermentation Tank - 12 Hour | 33.937 | 45,405 | 24.915 | 9,275,953 |
| Fermentation Tank - 14 Hour | 32.136 | 156,097 | 24.993 | 9,194,936 |
| Fermentation Tank - 16 Hour | 32.932 | 95,546 | 25.138 | 7,894,178 |
| Fermentation Tank - 18 Hour | 32.682 | 109,491 | 25.129 | 8,330,031 |
| Fermentation Tank - 20 Hour | 32.284 | 138,780 | 25.277 | 7,466,743 |
| Fermentation Tank - 22 Hour | 32.453 | 130,582 | 25.045 | 8,870,269 |
| Fermentation Tank - 24 Hour | 32.300 | 138,003 | 24.618 | 11,899,099 |
| Fermentation Tank - Drop (53 hour) | 31.956 | 181,752 | 24.880 | 10,179,281 |
| Beer Well 1 | 31.967 | 181,468 | 24.167 | 16,128,984 |
| Beer Well 2 | 31.190 | 301,330 | 25.398 | 6,968,052 |
| Whole Stillage | 38.409 | 2,330 | 34.106 | 16,636 |
| Thin Stillage | 34.301 | 35,710 | 29.135 | 495,358 |

In samples prepared by a filtering method of the present teachings, significant increases of sensitivity in the detection of *Lactobacillus* in corn mash samples were observed through the fermentation process, compared to samples prepared by the TSP method. The increased detection sensitivity of a sample prepared by a filtering method compared to the TSP method could be observed, for example, in samples obtained at time points considered crucial testing periods (Fermentation Tank Samples T=0 through T=18 hour), e.g., at time intervals during which antibiotics can be added to control lactic acid bacterial growth that would otherwise reduce ethanol production. Based on the differences in Ct values, *Lactobacillus* detection in the samples prepared by a filtering method of the present teachings compared to a TSP method had at least a 10-fold increase in sensitivity (Ct value difference of 4.024 as seen for Liquefaction Tank), with up to over a 1000-fold increase in sensitivity (Ct value difference of 12.717 as seen for Fermentation Tank—4 Hour).

Example 3: The Extraction, Detection and Quantification of *Lactobacillus* DNA from Samples of Corn Mash with Comparison of Data to Corresponding Acid Levels This example illustrates the extraction, detection and quantification of *Lactobacillus* DNA from samples of corn mash. This example also compares the quantification data as reported by the LAB PCR assay to the resulting lactic and acetic acid production across a 60 hour fermentation.

The fermentation was inoculated using six *Lactobacillus* cultures, each having a concentration of $10^3$ CFU/ml. The liquefaction pH was not adjusted, having an approximate pH of 5.1. Once again the reagent concentrations in the yeast prop and fermentation protocols were tweaked to closer resemble an actual fermentation batch. *Lactobacillus* CFU/ml quantities along with correlating lactic and acetic acid production was collected from 28 time points over the length of the fermentation (60 hours).

At the specified time points, mash was transferred from the fermentation flask using the port located at the bottom of the flask into a pre-assembled syringe filter. After collection, samples were filtered through the syringe into a tube according to the present teachings. Subsequent DNA extraction was performed using the newly developed extraction procedure as detailed in the present teachings. DNA extracts were assayed for the presence of *Lactobacillus* using the LAB PCR assay as detailed within the present teachings. Ct values were extrapolated into quantities based on the LAB RP L_fermentum_032318_1RT and LAB CLX All 6 Lacto_081618_5RT standard curves.

Figure 4:
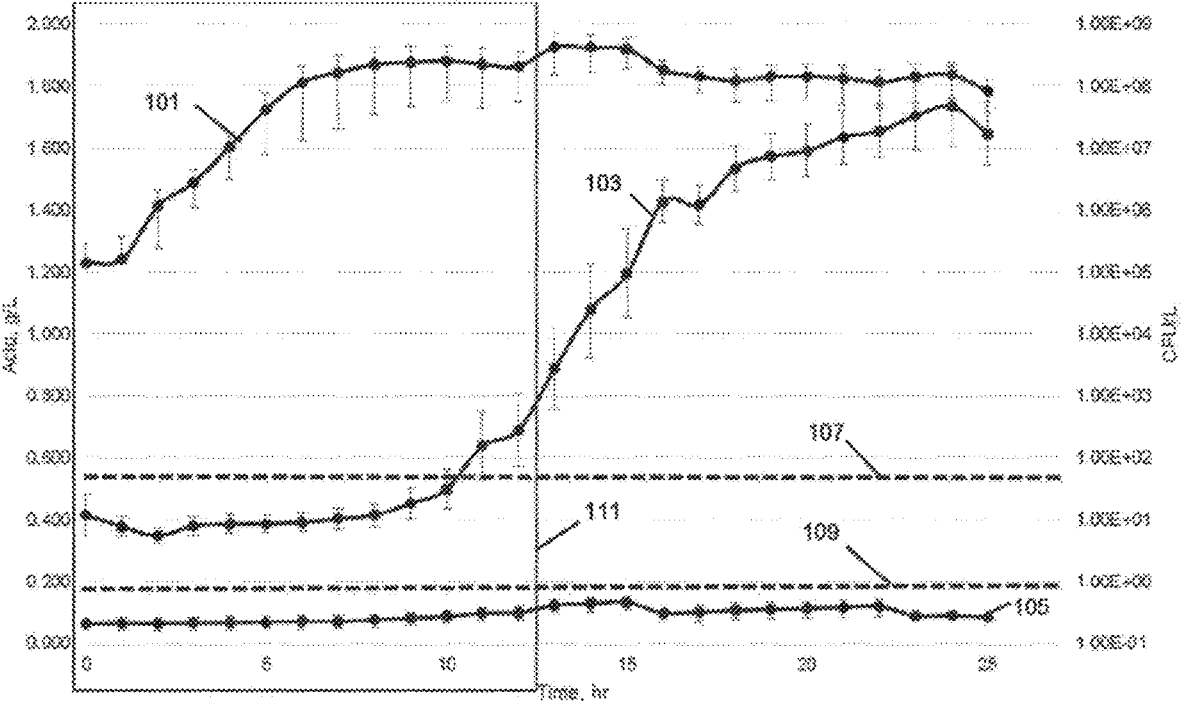
FIG. 4 is a graph displaying the average LAB bacterial quantity, lactic acid quantity, and acetic acid quantity at hourly time points of sampled corn mash from the first 25 hours of a fermentation process.

As depicted in FIG. 4, in a graph showing bacterial and acid profiles, a 2-3 order of magnitude increase was seen in the lactic acid bacterial levels 101 over the course of the first 25 hours. Line 103 refers to the lactic acid concentration, while line 105 depicts the acetic acid concentration. The dashed lines in the graph indicate the lactic acid threshold 107 and acetic acid threshold 109 that the industry considers undue stress to the yeast.

The graph depicted in FIG. 4, shows the first 25 hours of the fermentation process. In the ethanol industry, it is generally recommended to control any infections by the time the fermentation reaches 12-16 hours, as indicated by the box 111. FIG. 4 illustrates the bacteria levels 101 are increasing by hour two of the fermentation, whereas the traditional monitoring of lactic and acidic acids, 103 and 105, do not cross the industry thresholds 107 and 109 until the eleventh hour of the fermentation process.

The LAB assay is thus demonstrated to be able to detect the *Lactobacillus* bacteria within the mash samples and track the increase in bacterial cells across hourly time points. Accordingly, a method to quantitate LAB bacterial loads is herein provided when other indicators (i.e. lactic and acetic acid levels) are fundamentally non-existent.

What is claimed is:

1. A composition of DNA oligonucleotides comprising:
   i) a forward primer having a nucleotide sequence of at least 80% sequence identity to GGAGGCAGCAGTAGGGAATC (SEQ ID NO: 1);
   ii) a reverse primer having a nucleotide sequence of at least 80% sequence identity to ACCGCTACACATG-GAGTTCC (SEQ ID NO: 6); and,
   iii) a PCR probe comprising a fluorophore and at least one quencher, the PCR probe having a nucleotide sequence of at least 80% sequence identity to one of GCGGTAATACGTAGGTGGCA (SEQ ID NO: 4) or GCGGTAATACGTATGTTCCA (SEQ ID NO: 9).

2. A method for quantification of *Lactobacillus, Pedio-coccus* and *Weissella* bacteria, or one or some sub-combination thereof, in a sample of interest, suspected of containing lactic acid bacteria (LAB) nucleic acid comprising:
   obtaining the sample of interest from an ethanol fermentation tank or a corn mash sampling; and,
   performing a nucleic acid based amplification assay and nucleic acid quantification of one or some sub-combination of *Lactobacillus, Pediococcus* and *Weissella* bacteria of the sample of interest, wherein the nucleic acid based amplification assay provides:
   i) a forward primer having a nucleotide sequence selected from the group consisting of lactic acid bacteria (LAB) hybridizing sequence consisting of at least 80% to sequence identity GGAGGCAGCAGTAGGGAATC (SEQ ID NO: 1)

ii) a reverse primer having a nucleotide sequence selected from the group consisting of an LAB hybridizing sequence consisting of at least 80% sequence identity to ACCGCTACACATGGAGTTCC (SEQ ID NO: 6) and, iii) a PCR probe comprising a fluorophore, at least one quencher, and an oligonucleotide having a nucleotide sequence of at least 80% sequence identity to one of GCGGTAATACGTAGGTGGCA (SEQ ID NO: 4) or GCGGTAATACGTATGTTCCA (SEQ ID NO: 9).

3. The composition of DNA oligonucleotides of claim 1 wherein the PCR probe has a nucleotide sequence of at least 80% sequence identity to GCGGTAATACGTAGGTGGCA (SEQ ID NO: 4).

4. The composition of DNA oligonucleotides of claim 1 wherein the PCR probe has a nucleotide sequence of at least 80% sequence identity to GCGGTAATACGTATGTTCCA (SEQ ID NO: 9).

5. The method of claim 2 wherein the nucleic acid based amplification assay provides: a nucleotide sequence of at least 80% sequence identity to GCGGTAATACGTAGGTGGCA (SEQ ID NO: 4).

6. The method of claim 2 wherein the nucleic acid based amplification assay provides: a nucleotide sequence of at least 80% sequence identity to GCGGTAATACGTATGTTCCA (SEQ ID NO: 9).

* * * * *

SEQUENCE LISTING

```
<160> NUMBER OF SEQ ID NOS: 9

<210> SEQ ID NO 1
<211> LENGTH: 20
<212> TYPE: DNA
<213> ORGANISM: Artificial Sequence
```

-continued

```
<220> FEATURE:
<223> OTHER INFORMATION: SYNTHESIZED PRIMER OR PROBE DNA OLIGOMER

<400> SEQUENCE: 1
ggaggcagca gtagggaatc                                              20

<210> SEQ ID NO 2
<211> LENGTH: 20
<212> TYPE: DNA
<213> ORGANISM: Artificial Sequence
<220> FEATURE:
<223> OTHER INFORMATION: SYNTHESIZED PRIMER OR PROBE DNA OLIGOMER

<400> SEQUENCE: 2
tgaagaaggg tttcggctcg                                              20

<210> SEQ ID NO 3
<211> LENGTH: 20
<212> TYPE: DNA
<213> ORGANISM: Artificial Sequence
<220> FEATURE:
<223> OTHER INFORMATION: SYNTHESIZED PRIMER OR PROBE DNA OLIGOMER

<400> SEQUENCE: 3
tgccacctac gtattaccgc                                              20

<210> SEQ ID NO 4
<211> LENGTH: 20
<212> TYPE: DNA
<213> ORGANISM: Artificial Sequence
<220> FEATURE:
<223> OTHER INFORMATION: SYNTHESIZED PRIMER OR PROBE DNA OLIGOMER

<400> SEQUENCE: 4
gcggtaatac gtaggtggca                                              20

<210> SEQ ID NO 5
<211> LENGTH: 20
<212> TYPE: DNA
<213> ORGANISM: Artificial Sequence
<220> FEATURE:
<223> OTHER INFORMATION: SYNTHESIZED PRIMER OR PROBE DNA OLIGOMER

<400> SEQUENCE: 5
tgtccggatt tattgggcgt                                              20

<210> SEQ ID NO 6
<211> LENGTH: 20
<212> TYPE: DNA
<213> ORGANISM: Artificial Sequence
<220> FEATURE:
<223> OTHER INFORMATION: SYNTHESIZED PRIMER OR PROBE DNA OLIGOMER

<400> SEQUENCE: 6
accgctacac atggagttcc                                              20

<210> SEQ ID NO 7
<211> LENGTH: 20
<212> TYPE: DNA
<213> ORGANISM: Artificial Sequence
<220> FEATURE:
<223> OTHER INFORMATION: SYNTHESIZED PRIMER OR PROBE DNA OLIGOMER

<400> SEQUENCE: 7
acgcttgcca cctacgtatt                                              20
```

-continued

```
<210> SEQ ID NO 8
<211> LENGTH: 20
<212> TYPE: DNA
<213> ORGANISM: Artificial Sequence
<220> FEATURE:
<223> OTHER INFORMATION: SYNTHESIZED PRIMER OR PROBE DNA OLIGOMER

<400> SEQUENCE: 8
aacgcttgcc acctacgtat                                          20

<210> SEQ ID NO 9
<211> LENGTH: 20
<212> TYPE: DNA
<213> ORGANISM: Artificial Sequence
<220> FEATURE:
<223> OTHER INFORMATION: SYNTHESIZED PRIMER OR PROBE DNA OLIGOMER

<400> SEQUENCE: 9
gcggtaatac gtatgttcca                                          20
```